United States Patent [19]
Hausheer et al.

[11] Patent Number: 5,866,169
[45] Date of Patent: Feb. 2, 1999

[54] FORMULATIONS AND METHODS OF USE OF 2,2'-DITHIO-BIS-ETHANE SULFONATE

[75] Inventors: Frederick Herman Hausheer, Fair Oaks Ranch; Kochat Haridas, San Antonio; Dhanabalan Murali, San Antonio; Dasharatha Gauravaram Reddy, San Antonio; Seetharamulu Peddaiahgari, San Antonio, all of Tex.

[73] Assignee: BioNumerik Pharmaceuticals, Inc., San Antonio, Tex.

[21] Appl. No.: 878,244

[22] Filed: Jun. 18, 1997

Related U.S. Application Data

[60] Division of Ser. No. 553,005, Nov. 3, 1995, which is a continuation-in-part of Ser. No. 338,379, Nov. 14, 1994, Pat. No. 5,789,000.

[51] Int. Cl.$^6$ ...................................................... A61K 33/24
[52] U.S. Cl. .............................................................. 424/469
[58] Field of Search ............................................. 424/649

[56] References Cited

U.S. PATENT DOCUMENTS 5,789,000   8/1998   Husheer et al. .......................... 424/649

OTHER PUBLICATIONS

Leeuwenkamp et al. European Joural of Cancer, vol. 27, No. 10, pp. 1243–1247, Oct. 1991.

*Primary Examiner*—Richard L. Raymond
*Attorney, Agent, or Firm*—Thomas J. Dodd

[57] ABSTRACT

This invention describes novel formulations containing a water soluble disulfide, 2,2'-dithio-bis-ethane sulfonate, with or without cis-diammine dichloro platinum present in the same formulation, wherein the parenteral or oral administration of 2,2'-dithio-bis-ethane sulfonate is used to reduce the risk or prevent or retard the development of cisplatin induced nephrotoxicity, myelosuppression, and neurotoxicity, and wherein the parenteral or oral administration of 2,2'-dithio-bis-ethane sulfonate potentiates the antitumor activity of cisplatin when treating human patients with cancer. This invention also teaches novel formulations containing 2,2'-dithio-bis-ethane sulfonate alone or in combination with cisplatin in lyophilized or dissolved in an aqueous formulations which can be administered to patients with cancer who are being treated with cisplatin. The invention also teaches methods of preparing said formulations and their use in preventing cisplatin related toxicities and potentiation of cisplatin antitumor activity.

3 Claims, 4 Drawing Sheets

FORMULATIONS AND METHODS OF USE OF 2,2'-DITHIO-BIS-ETHANE SULFONATE

This Application is a division of application number 08/553,005, filed Nov. 3, 1995, pending which is a continuation-in-part of U.S. patent application Ser. No. 08/338,379 filed on Nov. 14, 1994, now U.S. Pat. No. 5,789,000.

BACKGROUND OF THE INVENTION

1. Field of the Invention

This invention teaches novel compositions and methods of use thereof, of a water soluble disulfide, 2,2'-dithio-bis-ethane sulfonate (also known as "disodium 2,2'-dithio-bis-ethane sulfonate", "dimesna" or "BNP7787") in human patients who are being treated for cancer with cis-diammine dichloro platinum (also known as "cisplatin" or "CDDP") and wherein cis-diammine dichloro platinum and 2,2'-dithio-bis-ethane sulfonate compositions are administered prior to, simultaneously or following the administration of cisplatin to reduce the risk of cisplatin induced nephrotoxicity when treating human patients with cancer. This invention also teaches the use of said compositions containing 2,2'-dithio-bis-ethane sulfonate as a key ingredient for the purposes of potentiating the antitumor activity of cisplatin in human subjects with cancer, and protecting against cisplatin related neurotoxicity and myelosuppression. In its preferred aspect, this invention involves the preparation and administration of a sterile, aqueous composition of 2,2'-dithio-bis-ethane sulfonate to human patients with cancer who are being treated with cisplatin. In another preferred form, this invention involves the preparation and administration of a lyophilized composition of 2,2'-dithio-bis-ethane sulfonate, which is reconstituted with aqueous media prior to administration to human patients with cancer who are being treated with cisplatin. This invention also teaches methods of administration of the claimed 2,2'-dithio-bis-ethane sulfonate compositions lacking cisplatin that can be carried out within 24 hours preceding and within 24 hours following the administration of cisplatin. Yet another aspect of this invention is the methods of simultaneous administration of cis-diammine dichloro platinum and 2,2'-dithio-bis-ethane sulfonate wherein the 2,2'-dithio-bis-ethane sulfonate is administered simultaneously with the administration of cis-diammine dichloro platinum. This simultaneous administration can be carried out by administering aqueous or lyophilized and reconstituted compositions containing 2,2'-dithio-bis-ethane sulfonate and cisplatin or by the simultaneous administration of each drug via separate routes of administration. Another aspect of this invention is a method of reducing cis-diammine dichloro platinum induced nephrotoxicity, neurotoxicity, and myelosuppression and also potentiating cisplatin antitumor activity in human patients whose cancer is optimally treated with cis-diammine dichloro platinum.

This invention describes novel aqueous and lyophilized compositions and methods of use thereof of a water soluble disulfide, 2,2'-dithio-bis-ethane sulfonate and disodium 2,2'-dithio-bis-ethane sulfonate, which has been discovered by the inventors to protect against cisplatin induced nephrotoxicity. The inventors also teach the use of 2,2'-dithio-bis-ethane sulfonate as a key ingredient of the claimed compositions for the purposes of preventing or retarding the development of cisplatin induced neurotoxicity and myelosuppression. The inventors have made the unexpected discovery that 2,2'-dithio-bis-ethane sulfonate also appears to potentiate (increase) the antitumor activity of cisplatin in vivo and accordingly claim the use of 2,2'-dithio-bis-ethane sulfonate for the purpose of increasing the antitumor activity of cisplatin. The novel lyophilized and aqueous compositions contain 2,2'-dithio-bis-ethane sulfonate or disodium 2,2'-dithio-bis-ethane sulfonate, with or without cis-diammine dichloro platinum and the invention teaches that 2,2'-dithio-bis-ethane sulfonate, and pharmaceutically acceptable salts thereof, may be administered simultaneously with or separately from cisplatin to reduce the risk of cisplatin induced toxicities when treating human patients with cancer.

2. Description of the Related Art

A. Introduction

The use of cytotoxic anticancer drugs pose an increased risk of certain drug related toxic side effects in human subjects undergoing cancer treatment. Drug toxicity associated with the use of anticancer drugs greatly limits their clinical utility and safety in human subjects. For example, drug-induced impairment of cellular and/or organ functions may result in organ-specific toxicities in human subjects being treated for cancer. Additionally, the drugs themselves or their metabolites may accumulate or damage certain cellular components or impair certain biochemical reactions in specific organs. The toxicities observed due to the administration of anticancer drugs are usually dose dependent (e.g., busulfan induced myelosuppression), are often related to cumulative dosages administered (e.g., BCNU induced pulmonary toxicity; anthracycline induced cardiac toxicity), and idiosyncratic drug toxicities are noted with some frequency with certain anticancer drugs (e.g., mitomycin-C induced hemolytic uremic syndrome). By impairing or damaging normal cellular function in specific organs the anticancer drug is causally connected with the drug-induced organ damage.

As a result of drug induced toxicity associated with the administration of anticancer drugs to humans, clinicians attempt to prevent or reduce the risk of drug toxicity by certain pharmacologic maneuvers. Such clinical maneuvers can impose risk of additional side effects, or result in a dose reduction of the anticancer drug which in turn may adversely affect the likelihood of achieving control of the patient's tumor. If the major dose-limiting organ toxicity of a particular anticancer drug is eliminated or substantially reduced, the result is that the safety and efficacy of the primary anticancer drug is greatly increased. A significant reduction in drug toxicity in cancer treatment generally results in greater ability to administer higher doses of the drug, prevents or reduces the number of treatment delays, and increases the safety and the quality of life for patients. An example of this approach is the use of G-CSF to reduce the duration and magnitude of drug induced myelosuppression resulting from the administration of several different types of anticancer drugs. Therefore, an important area of drug research and treatment is aimed at developing new methods to prevent or reduce drug induced dose limiting toxicities in human cancer patients.

This invention teaches new art which uses 2,2'-dithio-bis-ethane sulfonate or pharmaceutically acceptable salts thereof (including disodium 2,2'-dithio-bis-ethane sulfonate) contained in compositions which can be administered to human subjects with cancer being treated with cis-diammine dichloro platinum. For the purposes hereof, the useful composition of matter defined by this invention includes 2,2'-dithio-bis-ethane sulfonate, pharmaceutically acceptable salts of 2,2'-dithio-bis-ethane sulfonate, dimesna and BNP7787. The inventors have made an unexpected discovery that the use of compositions containing 2,2'-dithio-bis-ethane sulfonate are effective and safe in protecting against cis-diammine dichloro platinum induced nephrotoxicity (impairment of normal renal function). The inventors have also discovered that the administration of 2,2'-dithio-bis-ethane sulfonate compositions is safe and non-toxic and appears to provide protection against cisplatin induced myelosuppression, neurotoxicity and further appears to potentiate the antitumor activity of cisplatin. Myelosuppression is defined as the suppression of the production of blood cells from the bone marrow. Cisplatin neurotoxicity can manifest as the impairment of peripheral sensory neural function (paresthesias, numbness, pain), impairment of central neural function (including nausea, vomiting, ototoxicity, cranial nerve and ocular toxicities. For the purposes of this invention, cis-diammine dichloro platinum is also referred to as "cisplatin" and "CDDP" interchangeably and without restriction. The instant invention which encompasses novel compositions and methods of use of 2,2'-dithio-bis-ethane sulfonate has tremendous utility in preventing, retarding the development of and reducing the risk of these cisplatin induced toxicities in human patients with cancer. This invention also teaches methods of manufacture of said compositions in the instant invention containing the water soluble disulfide 2,2'-dithio-bis-ethane sulfonate (or pharmaceutically acceptable salts thereof) alone or in combination with other medicaments, when desired and add additional utility to this invention.

B. Cis-Diammine Dichloro Platinum (1) Background of Cis-Diammine Dichloro Platinum Cis-diammine dichloro platinum (referred herein to as "cisplatin" or "CDDP") is a widely used anticancer drug which is used in combination with other anticancer drugs in the treatment of cancers of the lung, breast, head and neck, ovary, esophagus, bladder, and testis. Along with its potent anticancer properties, cisplatin also has demonstrated clinically significant toxicities which limit its clinical utility and pose certain serious risks to patients undergoing treatment for cancer. The therapeutic benefits of cisplatin must always be carefully weighed against the possibility of these significant drug related toxicities associated with its use. It is well known that one of the most important and common dose limiting toxicities of cis-diammine dichloro platinum is renal damage in patients receiving this drug for treatment of their cancer. Neurotoxicity and myelosuppression are also important toxicities relating to cisplatin therapy in human patients (Perry, M. C., (1992) The Chemotherapy Source Book, Williams and Wilkins, 1172 pp.).

A stable and sterile aqueous solution of cisplatin in a sealed ampoule or vial containing a unit dosage form suitable for intravenous administration to a human patient with cancer was described in U.S. Pat. No. 4,310,515, entitled "Pharmaceutical Compositions of Cisplatin" (Issued Jan. 12, 1982). The patent claims cisplatin provided in a concentration between about 0.1 and about 1.0 mg/ml and a pH in a range of 2.0 to 3.0. The sterile aqueous cisplatin solutions may also contain sodium chloride and mannitol. The present invention claims aqueous compositions containing 2,2'-dithio-bis-ethane sulfonate alone or with any of the following components, in any combination without restriction: (a) sterile water for injection, (2) saline solutions with NaCl concentrations of about 0.1 to about 2.5%, (c) cisplatin in a concentration of about 0.1 to 1.0 mg/ml, (d) sufficient quantities of formulation hydrochloric acid or phosphoric acid to maintain the pH of said formulation in a pH range of about 2.0 to about 6.0, (e) pharmaceutical buffers such as sodium acetate or phosphate, and (f) mannitol in a concentration of about 1.0 to about 2.5%. The present invention also claims lyophilized formulations containing 2,2'-dithio-bis-ethane sulfonate and pharmaceutically acceptable salts thereof alone or in combination with any of the following without restriction: (a) cisplatin, (b) NaCl, (c) mannitol, (d) phosphoric acid, and (e) pharmaceutical buffers such as sodium acetate or phosphate. The present invention claims compositions and methods of use of said compositions which contain 2,2'-dithio-bis-ethane sulfonate in lyophilized or aqueous compositions that can be prepared and administered before, during or after the administration of cisplatin to human subjects with cancer.

(2) Mechanisms of Action of Cis-Diammine Dichloro Platinum

Cisplatin exchanges chloride ions for nucleophilic groups such as RS-, R-S-$CH_3$, imidazole nitrogens and R-$NH_2$ to form linkages which can be very stable. In an aqueous solution, one or both chloride ions may be replaced by water to produce a hydrated intermediate known as an "aquo cisplatin" species (See Reactions 1 and 2 below). The water molecule(s) attached to the cisplatin can be subsequently eliminated by an incoming nucleophile. In some cases there can be direct displacement of the chloride ion by an incoming nucleophile without the participation of the solvent. Thus, several species of cisplatin ("Pt") exist in solution as defined according to the following equilibria:

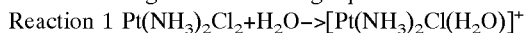
Reaction 1 $Pt(NH_3)_2Cl_2 + H_2O \rightarrow [Pt(NH_3)_2Cl(H_2O)]^+$

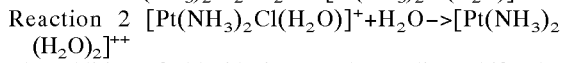
Reaction 2 $[Pt(NH_3)_2Cl(H_2O)]^+ + H_2O \rightarrow [Pt(NH_3)_2(H_2O)_2]^{++}$ The addition of chloride ions to the medium shifts the equilibrium to the left and the reactivity of the cisplatin species depends on the chloride concentration of the medium. Isotonic and hypertonic saline solutions have high chloride ion concentrations and cisplatin will predominate as the $Pt(NH_3)_2Cl_2$ species. The displacement of chloride ions from $Pt(NH_3)_2Cl_2$ in an environment with a high chloride concentration occurs very slowly over time with exposure to the strongest nucleophiles, such as the sulfur anion. For example, formulation of cisplatin with sodium thiosulfate or 2-mercapto ethane sulfonate (mesna) is impractical because of the chemical quenching of cisplatin with the sulfur anion or the sulfhydryl moiety of thiosulfate and mesna, respectively. Cisplatin is also directly incompatible with diethyldithiocarbamate due to the presence of the sulfur anion, and thus cannot be formulated in the same solution for parenteral administration.

Cisplatin is believed to act on tumor cell DNA by forming intrastrand crosslinks of the drug attaching to the N7 atom of the imidazole between adjacent purine bases comprising predominantly sequences of 5'-GG-3', 5'-AG-3', 5'-GA-3' or 5'-GXG-3' where X is a naturally occurring purine or a pyrimidine (e.g., adenine, thymine, cytosine or guanine) (Eastman, A., Biochemistry, 25, 3912–3915, 1986; Pinto, A. L. and Lippard, S., Biochem. Biophy. Acta, 780, 167–180, 1986). Cisplatin is believed to exert its antitumor effects by the formation of intrastrand crosslinks which may result in alterations in DNA structure or function. In order for cisplatin to react with certain nucleic acid sequences in cellular DNA, it must first undergo chemical conversion to an active species by the displacement of chloride ligands with water to form the mono-aquo or di-aquo species. The aquo species of cisplatin is reactive with nucleophilic species, including the imidazole nitrogens on DNA or sulfhydryl groups which are also present in cells forming the renal tubular epithelium in humans.

Cisplatin readily reacts with compounds containing sulfhydryl moieties. Sulfhydryl groups are found in cysteine, glutathione, and homocysteine. Metallothionein is a 7 kDa protein which has a high (approximately 30%) cysteine content Kelly, S. L. et al., *Science*, 241, 1813–1815, 1988). Increased cellular concentrations of metallothionein and glutathione have been correlated with drug resistance to cisplatin therapy. Thus, if the local renal tubular concentration of sulfhydryl groups from 2-mercapto ethane sulfonate is increased, then cisplatin toxicity may be reduced by the chemical quenching of the cisplatin aquo species in the renal tubules. The present invention accomplishes this objective.

The claimed invention teaches a new discovery in direct contrast to previously reported views of the pharmacology and metabolism of 2-mercapto ethane sulfonate (mesna). For the purposes of this invention, the administration of 2,2'-dithio-bis-ethane sulfonate preceding, following or simultaneously with cisplatin administration provides a physiologically safe source of additional sulfhydryl groups in the proximal and distal convoluted tubules to prevent renal toxicity. Unlike mesna, 2,2'-dithio-bis-ethane sulfonate is chemically inert with respect to cis-diammine dichloro platinum, and thus is compatible in the claimed formulation.

In the present invention, the chemical and pharmacologic behavior of parenterally or orally administered 2,2'-dithio-bis-ethane sulfonate is substantially different from the parenteral or oral administration of mesna as follows:

1. The 2,2'-dithio-bis-ethane sulfonate contained in the composition remains largely intact in the plasma;
2. 2,2'-dithio-bis-ethane sulfonate is a dianionic species and enters cells to a much lesser degree than mesna-cysteine, mesna-glutathione, and mesna-homocysteine disulfide conjugates. Therefore, more disulfide is filtered and excreted via the renal route, making more thiols available for detoxification in the kidney relative to parenterally or orally administered mesna; and
3. In the kidney, 2,2'-dithio-bis-ethane sulfonate undergoes reduction by renal glutathione reductase and thiol transferase enzymes to form free 2-mercapto ethane sulfonate, which in turn reacts with aquo species of cisplatin resulting in renal excretion of non-toxic cisplatin -2-mercapto ethane sulfonate conjugates.

For the purposes of this invention, the simultaneous or separate administration of cisplatin with 2,2'-dithio-bis-ethane sulfonate will provide a physiologically safe source of additional sulfhydryl groups in the proximal and distal convoluted tubules to prevent renal toxicity. Unlike mesna, 2,2'-dithio-bis-ethane sulfonate is chemically inert under proper conditions with respect to cis-diammine dichloro platinum, and thus is compatible in claimed formulations, and additionally when convenient, 2,2'-dithio-bis-ethane sulfonate can be administered separately preceding or following the administration of cisplatin as claimed in this invention.

It has been previously reported that oral or parenteral administration of 2-mercapto ethane sulfonate (mesna) to mice, rats or humans results in spontaneous autoxidation of mesna to form 2,2'-dithio-bis-ethane sulfonate (dimesna) in the plasma. James and Rogers reported an HPLC assay for plasma thiols using an electrochemical detector (James, C. A. and Rogers, *Journal of Chromatography*, 382, 394–398, 1986). The inventors submit that by using the method of James and Rogers, the detection and chemical characterization of dimesna (the putative human plasma metabolite of mesna) is indirect because this method can not chemically distinguish between dimesna, mesna-cysteine, and mesna-homocysteine conjugates. The HPLC method of James and Rogers involved the reduction of the samples by sodium borohydride and the samples were subsequently assayed for thiols. The difference in concentration from the unreacted initial sample and the sample that had been reacted with sodium borohydride was used to determine the amount of what was thought to be dimesna in the plasma. The inventors contend that sodium borohydride would react with mesna-mesna, mesna-cysteine, mesna-glutathione, mesna-homocysteine conjugates and thus, they submit that the method of James and Rogers fails to distinguish and quantitate the relative amounts of these entities which would form as a consequence of mesna metabolism. Other investigators rely on a similar or identical method as used by James and Rogers. All of these reports fail to mention or take into account the possibility of mesna forming a significant proportion of thiol conjugates with entities other than mesna, e.g., mesna-cysteine, mesna-glutathione, mesna-homocysteine. The inventors submit that the method of James and Rogers is ambiguous, imprecise and not capable of specifically identifying the disulfide conjugate formed.

The inventors also note that increased cysteine elimination in the urine has been reported in association with the administration of mesna to human subjects (Sidau, B. and Shaw, I. C., *J. Chromatography*, 311, 234–238, 1984). This observation indirectly supports the inventors' current hypothesis of disulfide conjugation of mesna with other thiols in the plasma (FIG. 1, "New Hypothesis", Middle Column). The enhanced cysteine elimination in urine, as reported by Sidau et al., can be explained by the current invention. The inventors contend that a disulfide linkage forms between mesna and cysteine in the plasma and reduction by glutathione reductase and thiol transferase of the mesna-cysteine conjugates occurs in the renal tubular system to generate free thiols. The free thiols are predicted to react with toxic aquo metabolites of cisplatin.

In view of the above discussion, the inventors submit that the concurrent, pre- or post-administration of 2,2'-dithio-bis-ethane sulfonate with cisplatin is chemically and pharmacologically superior to using mesna because: (1) a greater amount of disulfides will be delivered to the renal tubular system whereupon these disulfides are available for reduction by glutathione reductase and thiol transferases to form the free thiol, 2-mercapto ethane sulfonate, and (2) a lower amount of energy is needed to reduce the 2,2'-dithio-bis-ethane sulfonate disulfide linkage which in turn will generate a greater amount of free thiols in the renal tubules whereupon these free thiols can react with the toxic aquo species of cisplatin.

An object of this invention is the simultaneous or separate, parenteral administration of 2,2'-dithio-bis-ethane sulfonate and cisplatin to human subjects with cancer. Another object of the present invention is the separate administration of 2,2'-dithio-bis-ethane sulfonate preceding or following the administration of cisplatin. Another object of this invention is oral or parenteral administration of 2,2'-dithio-bis-ethane sulfonate to human patients with cancer. Yet another object of this invention is the administration of 2,2'-dithio-bis-ethane sulfonate for the purpose of preventing, reducing or retarding the development of cisplatin related neurotoxicity, myelosuppression and the use of 2,2'-dithio-bis-ethane sulfonate for the purposes of potentiating (increasing) the antitumor activity of cisplatin in human subjects with cancer. The following characteristics of 2,2'-dithio-bis-ethane sulfonate support its use in the present invention:

1. 2,2'-dithio-bis-ethane sulfonate will predominate in the plasma compartment.
2. 2,2'-dithio-bis-ethane sulfonate is an anionic species because it has two negatively charged oxygens.

Because of this anionic characteristic, the molecule penetrates cell membranes, especially those of cancer cells, very poorly.

3. The highly anionic nature and small molecular size of 2,2'-dithio-bis-ethane sulfonate are key properties which account for its rapid and nearly exclusive excretion in high concentrations through the kidney.

4. In the absence of any other treatment, 2,2'-dithio-bis-ethane sulfonate has reportedly been tested only once in normal human volunteers (Shaw, I. C. and Weeks, M. S., *Eur J Cancer Clin Oncology* 23:933–935; 1987; Brock N., et al., *J. Cancer Res. Clin. Oncol.*, 108, 87–97, 1984; Brock N., et al., *Eur. J. Cancer Clin. Oncol.* 18, 1377–1387, 1982; Brock, N. et al., *Eur. J. Cancer Clin. Oncol.* 17, 1155–1163, 1981). However, the investigators in that instance failed to confirm the chemical identity of the metabolites in the plasma and urine of the human subjects. 2,2'-dithio-bis-ethane sulfonate has not been administered to human subjects being treated with platinum based therapies.

Cisplatin induced nephrotoxicity may be reduced because of the high local concentration of 2-mercapto ethane sulfonate that may be generated from 2,2'-dithio-bis-ethane sulfonate by renal tubular enzymes such as gamma glutamyl transpeptidase and thiol transferases in the same region of the renal tubules where the formation or delivery of a high concentration of aquo species of cisplatin is achieved. If cisplatin is conjugated with glutathione or other free thiols, these cisplatin conjugates are likely to be nephrotoxic if further metabolized to mercapturic acids (Hanigan M. H. et al. Cancer Research 54:5925; 1995). 2,2'-dithio-bis-ethane sulfonate, or its metabolite 2-mercapto ethane sulfonate, may prevent conjugation of cisplatin with glutathione or other endogenous thiols and/or further metabolism of cisplatin conjugates to mercapturic acids which are believed to be nephrotoxic.

This invention is also useful because the simultaneous or separate oral or parenteral administration of 2,2'-dithio-bis-ethane sulfonate and cisplatin: (1) insures treatment compliance, (2) will reduce pharmacy preparation costs, (3) will reduce errors in prescribing both drugs, (4) will reduce the amount of additional prophylactic maneuvers needed in order to reduce toxicity and avoid iatrogenic related complications (i.e. furosemide, or hypertonic saline administration as described above), and (5) for greater utility when a longer shelf life is desired, this invention also teaches methods to make and use lyophilized formulations containing 2,2'-dithio-bis-ethane sulfonate alone or in combination with cisplatin, mannitol, buffers and sodium chloride. 2,2'-dithio-bis-ethane sulfonate can be contained in a lyophilized formulations with other useful medicaments such as cisplatin, sodium chloride, mannitol, and buffers in any combination and without restriction.

Formulations of cisplatin and 2,2'-dithio-bis-ethane sulfonate must be maintained at a pH less than 7.0 and greater than 1.0 because of the need to prevent the formation of aquo species of cisplatin and also to prevent the formation of mesna which could subsequently react with cisplatin species. Another important component of this invention is the use of sufficiently high concentrations of NaCl (e.g., 0.9% or greater) and HCl because the stability of cisplatin is proportionally related to the chloride ion concentration of the solution.

C. Nephrotoxicity Associated with Cis-Diammine Dichloro Platinum Administration

One of the most important limitations in the human clinical use of cisplatin is the nephrotoxicity which develops as a consequence of cumulative and dose dependent exposure to the drug, or which may occur in setting the administration of cisplatin to patients with renal insufficiency or co-administration of other nephrotoxic agents (e.g., aminoglycosides) (Rozencweig et al., 1977, Cis-diamminedichloroplatinum (II), *Ann. Intern. Med.*, 86, 803; Gonzalez-Vitale et al., 1977, The renal pathology in clinical trials of cisplatin (II) diamminedichloride, *Cancer*, 39, 1362; Campbell et al., 1983, Plasma platinum levels: Relationship to cisplatin dose and nephrotoxicity, *Cancer Treat. Rep.,* 67, 169; Offerman et al., 1984, Acute effects of cis-diammine-dichloroplatinum (CDDP) on renal function, *Cancer Chemother. Pharmacol,* 12, 36).

The major clinical features of cisplatin induced nephrotoxicity include decreases in creatinine clearance, elevated creatinine, elevated BUN, elevated uric acid and hypomagnesemia. The dose limiting toxicity of cisplatin when administered as a single dose per cycle is nephrotoxicity. Nephrotoxicity associated with cisplatin administration may also be related to the peak plasma concentration of the drug. Hyperuricemia and hypoalbuminemia are predisposing factors to cisplatin nephrotoxicity along with renal insufficiency, concomitant administration of other drugs, including aminoglycoside antibiotics and possibly by amphotericin B.

Typical pathological changes in the kidneys after cisplatin application have been observed in laboratory animals and humans. (Kociba and Sleight, 1971, Acute toxicologic and pathologic effects of cis-diammine dichloro platinum in the male rat, *Cancer Chemother. Rep.*, 55, 1; Choie et al., 1981, Acute and chronic cisplatin nephropathy in rats, *Lab. Invest.*, 44, 397; Goldstein and Gilbert, 1983, The nephrotoxicity of cisplatin, *Life Sci.*, 32, 685). Certain strains of rats have been noted for their excellent correlation with human nephrotoxicity, including Fischer, Wistar, and Harlan-Sprague Dawley rats. These cisplatin induced renal lesions are dose and time dependent, and are mainly localized in the outer stripe of the medulla of the kidney, which corresponds to the microscopic anatomic location of the glomerulus and convoluted tubules.

Thus, cisplatin induced nephrotoxicity usually occurs as a result of the cumulative and dose dependent exposure to the drug, or when administered to patients with renal insufficiency or when coadministered with another nephrotoxic agent (e.g., aminoglycosides). The dose limiting toxicity of cisplatin, when the drug is administered as a single dose per cycle, is nephrotoxicity which may be related to the peak plasma concentration of the drug itself.

Cisplatin induced nephrotoxicity is a clinically important problem associated with the use of the drug, and certain clinical maneuvers are generally employed in an attempt to reduce the risk of this complication. These prophylactic maneuvers include:

a. Parenteral administration of hypertonic (3%) NaCl; (Ozols et al., 1984, High-dose cisplatin in hypertonic saline, *Ann. Intern. Med.*, 100, 19);

b. Parenteral administration of normal (0.9%) NaCl;

c. Mannitol diuresis (Hayes et al., 1977, High dose cisplatin diammine dichloride, amelioration of renal toxicity by mannitol diuresis, *Cancer*, 39, 1372);

d. Pre- and/or post treatment hydration (oral or parenteral);

e. Forced diuresis by the administration of loop diuretics such as furosemide (Ostrow et al., 1981, High-dose cisplatin therapy using mannitol versus furosemide diuresis: comparative pharmacokinetics and toxicity, *Cancer Treat. Rep.*, 65, 73); and f. Oral or parenteral administration of reduced thiols such as diethyldithiocarbamate (rodents), thiosulfate (humans), or 3-aminopropyl amino ethylphosphorothioic acid (WR-2721).

However, these maneuvers have certain drawbacks which limit the practical use of cisplatin and introduce additional definite risks for treatment related complications in patients undergoing treatment. For example, the administration of hypertonic saline (NaCl 3.0%) poses the risk of iatrogenic hypernatremia. Hypernatremia is a life threatening medical emergency which can be fatal, and the administration of hypertonic saline is contraindicated in patients with elevated serum sodium or patients with congestive heart failure. The administration of normal saline (NaCl 0.9%) in patients increases the risk of fluid overload in patients. The use of powerful loop diuretics to increase urine production by the kidney such as furosemide increase the iatrogenic risk of hypokalemia, hyponatremia, hypocalcemia, hypovolemia, metabolic alkalosis and hypochloremia. All of these conditions can be life threatening and in some cases are fatal.

It is important to note that these maneuvers aimed at prophylaxis of cisplatin nephrotoxicity require additional clinical services, additional patient monitoring (e.g., physicians, nurses, and pharmacists), and additional hospitalization expense. Additionally, since these prophylactic maneuvers (aimed at reducing the risk of nephrotoxicity) are separate from the administration of the drug (cis-diammine dichloro platinum), the patient runs the risk of experiencing additional toxicity due to the maneuver itself (e.g., fluid overload, congestive heart failure, hyperosmotic state, hypernatremia or by physician, nurse, pharmacist or support staff human error).

This invention reduces cisplatin induced nephrotoxicity, neurotoxicity and myelosuppression and potentiates the antitumor activity of cisplatin by the oral or parenteral administration of 2,2'-dithio-bis-ethane sulfonate to human subjects being treated with cisplatin for cancer therapy. The 2,2'-dithio-bis-ethane sulfonate and cis-diammine dichloro platinum are in compositions suitable for administration to human subjects with cancer, or alternatively 2,2'-dithio-bis-ethane sulfonate is administered separately from cisplatin. As discussed above, parenteral formulations of mesna (mercapto ethane sulfonate sodium) or sodium thiosulfate with cisplatin are not practical because the sulfhydryl groups on mesna or the sulfate anion of sodium thiosulfate will react with cisplatin yielding inactive species of cisplatin.

D. Water Soluble Thiols as Detoxifying Agents in the Kidney 1. 2-Mercaptoethane Sulfonate Sodium or "Mesna"

Mesna is a pharmacologically safe thiol that has been used clinically in human subjects for approximately two decades. Mesna has been reported to be rapidly eliminated through the kidneys, accumulates in the urine and, unlike cysteine or N-acetyl cysteine, only slightly penetrates cellular membranes. In the rat, over 80% of the administered dose of mesna is reportedly recovered in the urine within three hours after intravenous administration (Pohl et al., *Meth. Find. Clin. Pharmacol.* 3(Suppl 1), 95–101, 1981).

For the purposes of the present invention, the inventors wish to point out that the analytical methods previously used to detect the presence of mesna metabolite in the plasma or in the urine in the studies are incapable of determining the chemical identity of the thiol (see discussion above). Mesna is widely used to reduce or prevent the risk of hemorrhagic cystitis to the uroepithilium which is associated with the use of chloroethylnitrosoureas (including BCNU, CCNU and MeCCNU) and certain oxazaphosphorine type anticancer drugs which include cyclophosphamide, ifosfamide and trophosphamide. Mesna administered orally or parenterally to human subjects significantly reduces the incidence of uroepithelial toxicity in patients receiving therapy with these drugs. Oxazaphosphorine induced hemorrhagic cystitis can be a life threatening condition due to profuse bleeding from the uroepithelial surfaces involving the ureters, bladder and urethra.

It is especially important to note for the present invention that oxazaphosphorine or chloroethylating agent induced uroepithelial toxicity is chemically, biochemically, anatomically and pathologically distinct from the renal toxicity which is observed with administration of cisplatin. Cisplatin is an inorganic molecule whereas oxazaphosphorines and chloroethylating type anticancer drugs are organic molecules. The toxic species of cisplatin is the inorganic mono- and di-aquo species whereas the toxic species of oxazaphosphorines is the organic molecule, acrolein and for chloroethylating drugs are the chloroethyl intermediates. The toxic species of oxazaphosphorines and chloroethylating anticancer drugs are chemically distinct and result from entirely different precursors and produce damage in tissues which is clearly different from that of cisplatin and its metabolites. Cisplatin damages renal tubular cells whereas oxazaphosphorines and chloroethylating type anticancer drugs damage the uroepithelium (renal pelvis, ureters, bladder and urethra). It is also important to note that the organic chemical interactions of mesna with acrolein, the toxic species produced by the metabolism of anticancer oxazaphosphorines which directly damages the uroepithelium, is entirely different than the proposed inorganic chemical interactions which lead to detoxification of cisplatin by mesna.

Dimesna, the only reported metabolite of mesna, is reportedly formed spontaneously by autoxidation of mesna in the plasma. Mesna dimers (two mesna molecules covalently attached via a disulfide linkage) are reported to predominate in the blood following mesna administration. This mesna dimer metabolite is reportedly eliminated through the kidneys by glomerular filtration, being partly reduced to mesna during excretion (Brock, et al., *Arzneim Forsch*, 32, 486–487, 1982). Reportedly, an average of approximately 45% of the administered mesna dose is found in the urine in the form of mesna, the reactive thiol. The remainder found is reportedly a mesna metabolite, dimesna.

2. Bioavailability of Orally Administered Mesna In 1984, Burkert et al. described the bioavailability of orally administered mesna (sodium 2-mercaptoethane sulfonate, Uromitexan; Burkert et al., *Arzneim.-Forsch./Drug Res.* 34, 1597, 1984). Previous experimental studies in rats had demonstrated that mesna was absorbed from the intestine following oral administration and that it passed unchanged through the hepatic vascular system (Brock et al., *J. Cancer Res. Clin. Oncol.* 108, 87 1984; Ormstad et al., *Cancer Research*, 43, 333, 1983). It was proposed that in the plasma mesna was rapidly oxidized to disulfide dimesna and that the reaction occurs when mesna was injected intravenously. It was further proposed that after glomerular filtration, about 50% of dimesna was reduced to mesna in the renal tubular epithelium.

The inventors propose that it is unlikely that oral or parenterally administered mesna would necessarily be oxidized in the plasma to form significant quantities of dimesna (e.g., quantities greater than 40% of an administered dose). The inventors propose that the significant majority of mesna reacts with other plasma thiols to form conjugates with cysteine, glutathione and other thiol containing amino acids which are small enough to still undergo glomerular filtration and possibly tubular secretion and would be cleaved to form mesna (plus the free amino acid) in the tubular lumen. The inventors also specifically propose for the first time that mesna reacts predominantly with other thiols in the plasma such as cysteine, homocysteine, or the cysteine contained in glutathione (See above discussion). Since mesna forms a disulfide linkage with thiol containing amino acids or peptides it could still be filtered by the glomerulus or secreted in the proximal tubule. The therapeutic disadvantage of these mesna-cysteine and other similar disulfide conjugates is that their disulfide linkages are chemically more stable than the 2,2'-dithio-bis-ethane sulfonate conjugate proposed in the present invention, which results in a less facile chemical production of free thiols in the kidney.

In their study, Burkert et al. (Burkert et al., Bioavailability of orally administered mesna, *Arzneim.-Forsch./Drug Res.* 34, 1597, 1984) confirmed the established bioavailability of orally administered mesna with studies in healthy volunteers and patients with tumors. Burkert et. al. tested the oral administration of mesna (Uromitexan drink ampoules) in 18 healthy probands and in 5 tumor patients. Following a single oral administration of either 20 or 40 mg/kg mesna, approximately 52% of the dose was excreted in the urine as reactive thiol groups and the only metabolite of mesna, mesna disulfide or dimesna, comprised the remaining 48%. The experimental methods used to characterize mesna or dimesna in these studies are not conclusive in establishing with certainty the precise chemical identity of mesna or dimesna as urinary metabolites. It is far more likely that mesna was conjugated with certain thiols such as cysteine, homocysteine or glutathione. The key description used to characterize the identity of the putative dimesna metabolite by previous research groups is "thiol groups" which could represent other amino acids.

This study also concluded that after intravenous injection of 20 mg/kg mesna, about 48% of the dose administered appeared as thiol groups in the urine. It took approximately 13 hours (20 mg/kg p.o.) or 18 hours (40 mg/kg p.o.) for the concentration to drop below the minimum concentration presumed to still be protective (100 ug/ml). However, the elimination pattern and the time required to reach the threshold concentration of mesna varies dramatically from patient to patient.

3. Concomitant Use of Oral Mesna in Rats or Thiosulfate in Humans to Reduce the Urotoxic Effects Of the Cisplatin Kempf et al. studied the effects of per os administration of sodium 2-mercaptoethane-sulfonate (mesna) in rats in preventing the nephrotoxic effects of cisplatin administered intraperitoneally (Kempf et al., Effective prevention of the nephrotoxicity of cisplatin (CDDP) by administration of sodium 2-mercaptoethane-sulfonate (mesna) in rats, *Br. J. Cancer*, 52, 937–939, 1985). As described above, mesna is extensively used in patients who receive oxazaphosphorine antitumor drugs such as cyclophosphamide and ifosfamide to protect the urinary tract, especially the ureters and bladder, against the toxic organic metabolite, acrolein (Brock, et al., 1982). In the case of oxazaphosphorines, acrolein is produced as a result of their metabolism and mesna undergoes addition to the double bond of acrolein, resulting in a stable thioether adduct which has no damaging effects on the uroepithelium and is excreted in the urine.

For the purpose of this invention, it is important to distinguish that the acrolein metabolite, an organic molecule, of the oxazaphosphorines is associated with uroepithelial toxicity, and in absolute contrast, cisplatin and its aquo species, which are inorganic molecules, are associated with direct toxicity to the kidney (nephrotoxicity or renal toxicity). Therefore, the uses of 2-mercapto ethane sulfonate as a protective agent against oxazaphosphorine and chloroethylating agent associated toxicities are entirely different from the protective uses of 2,2'-dithio-bis-ethane sulfonate in the present invention.

Howell and colleagues (Howell et al., Intraperitoneal cisplatin with systemic thiosulfate protection, *Ann. Int. Med.*, 97, 845–851, 1982) administered thiosulfates by intravenous infusion to cancer patients receiving intraperitoneal cisplatin. They observed that much higher (more than two fold) doses of cisplatin per meter square could be administered intraperitoneally and that renal toxicity could be prevented when thiosulfates are administered by the intravenous route. The inventors note that the use of sodium thiosulfate in an aqueous formulation of cis-diammine dichloro platinum is not practical because thiosulfate will inactivate cisplatin and is incompatible in the same solution.

Protection against the nephrotoxicity of intraperitoneally administered cisplatin in rats through oral mesna administration has not been established until the work of Kempf et al. As stated above, mesna disulfide is the only reported metabolite of mesna and mesna disulfide does not readily react with electrophilic alkylating agents such as nitrogen mustard or oxazaphosphorines (Brock et al., The development of mesna for the inhibition of urotoxic side effects of cyclophosphamide, ifosfamide, and other oxazaphosphorine anticancer drugs, *Rec. Res. Cancer Res.*, 74, 270, 1980). After oral administration of mesna, the formation of dimesna reportedly occurs almost solely in the blood. After i.v. administration of mesna, the disulfide is reportedly spontaneously formed by autoxidation and found predominantly in the blood stream (Brock et al., Studies on the urotoxicity of oxazaphosphorine cytostatics and its prevention. *Eur. J. Cancer. Clin. Oncol.* 18, 1377, 1982). Brock and co-workers reported that dimesna is eliminated through the kidneys by glomerular filtration, and, to a great extent, reduced to mesna during excretion.

Using per os administration of mesna, Kempf et al. demonstrated complete prevention of renal damage in rats after a single i.p. dose of 3 mg cisplatin /kg body weight. Their data demonstrated a clear dose/effect relationship, in that low doses of mesna only partially protected the kidneys of rats from renal damage. The inventors wish to point out that 2-mercapto ethane sulfonate differs vastly from 2,2'-dithio-bis-ethane sulfonate on a physicochemical, biochemical, toxicological and pharmacologic basis in terms of formulation compositions and methods of use claimed in the instant invention.

The study of Kempf et al. notably involved the intraperitoneal administration of cisplatin with prior and subsequent oral administration of mesna in rats. The pharmacokinetics of intraperitoneally administered cisplatin differ substantially from the parenteral (e.g., intravenous) administration of cisplatin. In the case of intraperitoneal administration of cisplatin, it is possible to achieve much higher local (intraperitoneal) concentrations of cisplatin, and there is less risk of nephrotoxicity because intraperitoneal cisplatin and its various species do not achieve similar peak plasma concentrations to those achieved with intravenous administration of cisplatin. The oral administration of 2,2'-dithio-bis-ethane sulfonate is predicted by the inventors to be substantially different as follows: (a) intravenous or intraarterial administration of 2,2'-dithio-bis-ethane sulfonate is predicted to reach higher plasma concentrations and greater area under the curve values at given dosages relative to orally administered 2,2'-dithio-bis-ethane sulfonate, and (b) the plasma half life of 2-mercapto ethane sulfonate versus 2,2'-dithio-bis-ethane sulfonate will be different in humans. It is also important to note that at maximally tolerated dosages, the peak plasma concentration and the amount of cisplatin excreted by the kidney is less during intraperitoneal administration than the peak plasma concentration and amount of cisplatin excreted by the kidney when cisplatin is administered intravenously.

The experiments reported by Kempf et al. in rats completely fails to test or describe the ability of parenterally or orally administered 2,2'-dithio-bis-ethane sulfonate in humans to protect against any toxicities related to intravenously administered cisplatin. The inventors point out that there is no art which teaches the administration of 2,2'-dithio-bis-ethane sulfonate to humans with any type of platinum anticancer drug. Because of the above discussion and the literature, one could surmise that the simultaneous administration of mesna would result in the inactivation of cisplatin. Mesna is directly incompatible with cisplatin and is reported in the Physician's Desk Reference (p. 661 1994 Edition, Medical Economics Data Production Company). The inventors have determined that the parenteral administration of 2,2'-dithio-bis-ethane sulfonate and cisplatin can result in an increase in cisplatin nephrotoxicity at lower doses of 2,2'-dithio-bis-ethane sulfonate; this increase in toxicity can be overcome by administration of higher doses of 2,2'-dithio-bis-ethane sulfonate. This observation has not been reported before. Prior to this invention, one cannot predict that the simultaneous administration of 2,2'-dithio-bis-ethane sulfonate would or would not result in cisplatin inactivation or an increase in cisplatin toxicity. The inventors further believe that the administration of mesna does not result in the formation of substantial amounts of dimesna in the plasma; rather mesna predominantly forms conjugates with other plasma thiols, especially the amino acid cysteine which is abundant in the plasma (see above discussion). Additionally, the inventors have determined that the administration of 2,2'-dithio-bis-ethane sulfonate with cisplatin abrogates other cisplatin related toxicities, including myelosuppression and neurotoxicity. The inventors have also made the unexpected discovery that the administration of 2,2'-dithio-bis-ethane sulfonate can potentiate the antitumor activity of cisplatin. The 2,2'-dithio-bis-ethane sulfonate mediated abrogation of cisplatin induced myleosuppression and neurotoxicity, and the potentiation of cisplatin antitumor activity are new discoveries and have not been previously reported by others.

Thus, this invention is novel because: (1) novel methods of use involving the parenteral administration of cisplatin and oral or parenteral administration of 2,2'-dithio-bis-ethane sulfonate are claimed, (2) methods of making and using compositions of 2,2'-dithio-bis-ethane sulfonate alone or with cisplatin in sterile aqueous or lyophilized compositions wherein said compositions are suitable for use in human patients with cancer are claimed, (3) the present invention describes the use of 2,2'-dithio-bis-ethane sulfonate as a key ingredient for the purpose of retarding or abrogating the development of cisplatin induced nephrotoxicity, myelosuppression and neurotoxicity, and (4) the present invention teaches that 2,2'-dithio-bis-ethane sulfonate as a key ingredient can be used to potentiate the antitumor activity of cisplatin.

As stated above, this invention challenges the previous reports that mesna, to a large extent, forms dimesna in the plasma of humans. The inventors submit that oral or parenteral administration of mesna to human subjects results in the formation of more mesna-cysteine conjugates which are excreted by the kidney as compared to mesna-mesna conjugates. Cysteine, homocysteine and glutathione are endogenous thiols in human plasma and therefore could undergo reaction with mesna.

The inventors have also determined that the administration of 2,2'-dithio-bis-ethane sulfonate with cisplatin can result in protection against cisplatin induced myelosuppression and neurotoxicity, and have observed potentiation of the antitumor activity of cisplatin in tumor bearing animals. The inventors do not wish to be bound by any hypothetical explanation of the possible mechanisms of these beneficial effects of the administration of 2,2'-dithio-bis-ethane sulfonate in humans treated with cisplatin. The inventors postulate that the beneficial increase in antitumor activity in tumor bearing animals may be the result of altered pharmacokinetic behavior of cisplatin in the presence of 2,2'-dithio-bis-ethane sulfonate as a consequence of an increased peak plasma concentration or area under the curve of cisplatin, or a combination of the two pharmacokinetic parameters. Another hypothesis relating to the potentiation of the antitumor activity of cisplatin is that 2,2'-dithio-bis-ethane sulfonate is forming a complex with cisplatin that results in altered pharmacokinetic behavior of cisplatin in the form of any of the following parameters: increased effective tumor uptake of cisplatin, increased peak plasma concentrations of cisplatin or increased area under the curve of cisplatin.

SUMMARY OF THE INVENTION 2,2'-dithio-bis-ethane sulfonate, and pharmaceutically acceptable salts thereof, is the key ingredient of all the claimed compositions and uses thereof in the present invention. Pharmaceutically acceptable salts of 2,2'-dithio-bis-ethane sulfonate include: (a) disodium 2,2'-dithio-bis-ethane sulfonate, (b) monosodium 2,2'-dithio-bis-ethane sulfonate, (c) sodium potassium 2,2'-dithio-bis-ethane sulfonate, (d) dipotassium 2,2'-dithio-bis-ethane sulfonate, (e) calcium 2,2'-dithio-bis-ethane sulfonate, (f) magnesium 2,2'-dithio-bis-ethane sulfonate and (g) monopotassium 2,2'-dithio-bis-ethane sulfonate. Any of these salts may be used in the present invention, but the disodium, monosodium, calcium and magnesium salts are more preferred. When other salts of 2,2'-dithio-bis-ethane sulfonate are used in place of the disodium salt, the concentration or proportion of the sulfonate will be adjusted according, to molarity. 1 g of the disodium salt, 2,2'-dithio-bis-ethane sulfonate is equivalent to 4.63 millimoles of 2,2'-dithio-bis-ethane sulfonate anion. Hereinafter, the invention will be discussed with reference to aqueous compositions of disodium 2,2'-dithio-bis-ethane sulfonate, but the person skilled in the art will readily be able to use the principles of this invention in relation to other compositions containing salts of 2,2'-dithio-bis-ethane sulfonate or its anionic form.

Compositions containing cisplatin and 2,2'-dithio-bis-ethane sulfonate must be maintained at a pH less than 7.0 because of the need to prevent or retard the rate of formation of appreciable quantities of the aquo species of cisplatin and also to prevent or retard the formation of 2-mercapto ethane sulfonate which could subsequently react with cisplatin species. Aqueous or lyophilized compositions that can be reconstituted with a pharmaceutically acceptable aqueous diluent containing 2,2'-dithio-bis-ethane sulfonate that do not contain cisplatin can have a much broader pH range. The inventors have determined that the disulfide linkage contained within 2,2'-dithio-bis-ethane sulfonate is stable in a variety of aqueous environments (pure water or saline solutions) over a broad pH range, from pH 1.5 to 9.0. One preferred embodiment is a pH of 2,2'-dithio-bis-ethane sulfonate ranging from 4 to 9. Lyophilized formulations containing 2,2'-dithio-bis-ethane sulfonate alone or with cisplatin are stable for longer periods of time (months to years) than their aqueous counterparts. When cisplatin is formulated with 2,2'-dithio-bis-ethane sulfonate, this invention teaches that the addition of sufficiently high concentrations of NaCl or HCl are necessary because the stability of cisplatin is proportionally related to the chloride ion concentration of the solution.

One object of this invention is novel compositions which contain both cis-diammine dichloro platinum and 2,2'-dithio-bis-ethane sulfonate in the same composition, wherein said composition is provided as an aqueous composition or a lyophilized composition which are intended for use in human subjects with cancer. The lyophilized compositions containing 2,2'-dithio-bis-ethane sulfonate with or without cisplatin and chloride salts, acids or buffers are reconstituted with a pharmaceutically acceptable diluent prior to administration to human subjects with cancer. Examples of pharmaceutically acceptable aqueous diluents include Sterile Water for Injection USP, Dextrose 5% and Water for Injection USP, 0.9% NaCl for Injection USP, Dextrose 5% 0.9% NaCl for Injection USP, Lactated Ringer's Solution, and the like. Suitable acids for the instant invention can be selected from the group consisting of hydrochloric acid and phosphoric acid. Suitable buffers for the instant invention include acetate and phosphate buffers, which are used when desired to maintain the solution at a desired pH range.

DEFINITIONS

For the purpose of this invention, certain words and phrases are defined as follows:

"Stable" means that the solution will not undergo major (>1%) chemical conversion within a reasonable period of time (dependent upon the final pH of the formulation mixture).

The word "about" when used for pH, cisplatin concentration, 2,2'-dithio-bis-ethane sulfonate concentration, NaCl concentration, or mannitol concentration is defined as +/−1%.

"Approximately" is defined to include a range of plus or minus 1%

There are numerous "anticancer agents" but the inventors prefer the following to be used with the claimed invention: 5-FU, bleomycin, VP-16 (etoposide), doxorubicin, cyclophosphamide, ifosfamide, trophosphamide, leucovorin, taxol, methotrexate, vincristine and vinblastine.

"Amber vial" is any vial which protects the contents from exposure to fluorescent light.

"Aqueous formulations" is defined as medicaments and pharmaceutical preparations which are dissolved or suspended in water and are suitable for human use.

"Routes of administration" is defined to include parenteral drug administration (which includes intravenous, intraarterial, intraperitoneal, subcutaneous, intracavitary, intrapleural) and oral drug administration.

"Injectable" is defined to mean administered parenterally by hypodermic needle, cannula or catheter (which includes intravenous, intraarterial, intraperitoneal, subcutaneous, intracavitary,and intrapleural administration).

"Lyophilized", "lyophilize", "cryodessicated", "reconstituted", "reconstitute" or "reconstitutable" are used to describe certain compositions or formulations and are well known terms of art. A lyophilized composition or formulation in this invention must be reconstituted with aqueous diluents prior to administration.

"pharmaceutically acceptable salts" of 2,2'-dithio-bis-ethane sulfonate for purposes of this invention include: (a) disodium 2,2'-dithio-bis-ethane sulfonate, (b) monosodium 2,2'-dithio-bis-ethane sulfonate, (c) sodium potassium 2,2'-dithio-bis-ethane sulfonate, (d) dipotassium 2,2'-dithio-bis-ethane sulfonate, (e) calcium 2,2'-dithio-bis-ethane sulfonate, (f) magnesium 2,2'-dithio-bis-ethane sulfonate and (g) monopotassium 2,2'-dithio-bis-ethane sulfonate. Any of these salts may be used in the present invention, but the disodium, monosodium, calcium and magnesium salts are more preferred. When other salts of 2,2'-dithio-bis-ethane sulfonate are used in place of the disodium salt, the concentration or proportion of the sulfonate will be adjusted according to molarity. 1 g of the disodium salt, 2,2'-dithio-bis-ethane sulfonate is equivalent to 4.63 millimoles of 2,2'-dithio-bis-ethane sulfonate anion.

"Simultaneous", "simultaneously", "concurrent", and "concurrently" are defined as the administration of 2,2'-dithio-bis-ethane sulfonate and cisplatin from either: (1) a composition containing both drugs or (2) separate compositions containing either cisplatin or 2,2'-dithio-bis-ethane sulfonate commencing and concluding at the same time to a patient.

"Preceding" is defined as the administration of 2,2'-dithio-bis-ethane sulfonate within 24 hours before the commencement of administration of a dose of cisplatin.

"Following" is defined as the administration of 2,2'-dithio-bis-ethane sulfonate within 24 hours after the conclusion of the administration of a dose of cisplatin.

"Composition" is defined as a composition of matter.

"Formulation" is defined as a pharmaceutical preparation which contains a mixture of various excipients and key ingredients which provide a relatively stable, desirable and useful form of a drug. For this invention, "formulation" is included within the meaning of the term "composition".

"Substantially contemporaneous" is defined as the administration of compositions containing 2,2'-dithio-bis-ethane sulfonate as a key ingredient which are administered to the patient who will be or has been treated with cisplatin within 24 hours; the composition containing 2,2'-dithio-bis-ethane sulfonate is administered within 24 hours prior to, simultaneously and/or 24 hours following the administration of the subsequent component parts. For this invention, "shortly" means within 24 hours of the administration of cisplatin. Thus, as an example, a composition containing 2,2'-dithio-bis-ethane sulfonate formulation is administered at time X and cisplatin is administered to the patient within time X+24 hours. Another example would be the administration of 2,2'-dithio-bis-ethane sulfonate one hour before the administration of cisplatin, followed by the simultaneous administration of 2,2'-dithio-bis-ethane sulfonate and cisplatin, which is followed by the administration of 2,2'-dithio-bis-ethane sulfonate one hour after the completion of cisplatin administration in the same patient.

"Cisplatin", "cis-diammine dichloro platinum", and "CDDP" are used interchangeably.

"Injectable formulations" and injectable solutions" are used interchangeably.

"2,2'-dithio-bis-ethane sulfonate" is defined to include 2,2'-dithio-bis-ethane sulfonate and pharmaceutically acceptable salts of 2,2'-dithio-bis-ethane sulfonate (including, without limitation, dimesna).

"Dimesna" and "disodium 2,2'-dithio-bis-ethane suffonate" refer to the disodium salt of and "2,2'-dithio-bis-ethane sulfonate".

"Solution" a liquid which may or may not additionally contain dissolved chemical species. Examples of solutions include water, 0.9% NaCl in water for injection, dextrose 5%. and water for injection, and the like.

"Untreated or previously treated with an anticancer agent" is defined as a patient diagnosed with cancer who has not received treatment (untreated) or who has received treatment (previously treated) with cytotoxic or hormonal drug therapy directed at curing or palliating their malignancy or their malignant disease.

Aqueous Compositions Containing 2.2'-Dithio-Bis-Ethane Sulfonate

This invention teaches novel compositions containing a water soluble disulfide, 2,2'-dithio-bis-ethane sulfonate as a key ingredient, wherein the presence of the disulfide and the parenteral administration of the composition reduces the risk of cisplatin induced nephrotoxicity, myelosuppression, neurotoxicity and potentiates the antitumor activity of cisplatin when treating human patients with cancer. This invention also teaches novel, aqueous parenteral compositions containing cis-diammine dichloro platinum and the water soluble disulfide 2,2'-dithio-bis-ethane sulfonate for the purpose of treating patients with cancer and preventing, retarding the development of, and reducing the risk of developing cisplatin induced toxicities including nephrotoxicity, myelosuppression and myelosuppression in human patients with cancer. Another purpose of this invention is the use of 2,2'-dithio-bis-ethane sulfonate to potentiate the antitumor activity of cisplatin in human patients with cancer. This invention also teaches methods of preparation and use of aqueous compositions containing 2,2'-dithio-bis-ethane sulfonate alone. Additionally, this invention teaches the addition of certain ingredients to improve the utility of said aqueous compositions as desired.

One object of this invention is a stable aqueous solution which comprises 2,2'-dithio-bis-ethane sulfonate with or without any of the following ingredients, in any combination, and without restriction: cisplatin; chloride salts wherein the salt is sodium chloride; and pharmaceutical buffers selected from a group consisting of sodium acetate and/or phosphate; and hydrochloric acid. All of these ingredients are packaged in a unit dosage form in a sealed container. This composition is suitable for intravenous or intraarterial administration to human patients with cancer by the injection thereof from the container. The following desirable concentration ranges are included in the claimed injectable solution: the concentration of cis-diammine dichloro platinum is between about 0.1 mg/ml and about 1.0 mg/ml, the concentration of 2,2'-dithio-bis-ethane sulfonate is between 1 mg per ml and about 320 mg/ml, the concentration of sodium chloride is between 0.1% and 2.5% by weight of water, and the amounts of buffer (sodium acetate or phosphate) and hydrochloric acid are in an amount sufficient to maintain the pH in the range of 2.0 to 6.0. Another embodiment of this invention is the addition of mannitol in a concentration between about 1.0% to about 2.5% by weight of water to the above disclosed injectable solutions.

Furthermore, these injectable compositions can be given to a human patient with cancer who has not been treated with an anticancer agent (untreated) or this injectable solution can be given to a patient who has previously been treated or exposed to an anticancer agent(s). Also, this injectable solution can be administered to human patients with cancer in combination with another anticancer agent or agents. There are numerous "anticancer agents" but the inventors prefer the following to be used with the claimed invention: 5-FU, bleomycin, VP-16 (etoposide), doxorubicin, cyclophosphamide, ifosfamide, leucovorin, taxol, methotrexate, vincristine and vinblastine.

Aqueous Compositions Containing 2,2'-Dithio-Bis-Ethane Sulfonate Can Be Comprised Of:

(i) 2,2'-dithio-bis-ethane sulfonate and water.

(ii) 2,2'-dithio-bis-ethane sulfonate, NaCl, and water.

(iii) 2,2'-dithio-bis-ethane sulfonate, cisplatin, NaCl, and water.

(iv) 2,2'-dithio-bis-ethane sulfonate, cisplatin, NaCl, phosphoric acid, and water.

(v) 2,2'-dithio-bis-ethane sulfonate, cisplatin, NaCl, hydrochloric acid, and water.

(vi) 2,2'-dithio-bis-ethane sulfonate, cisplatin, NaCl, phosphoric acid, a buffer, and water.

(vii) 2,2'-dithio-bis-ethane sulfonate, cisplatin, NaCl, hydrochloric acid, a buffer, and water.

(viii) 2,2'-dithio-bis-ethane sulfonate, cisplatin, NaCl, phosphoric acid, mannitol and water.

(ix) 2,2'-dithio-bis-ethane sulfonate, cisplatin, NaCl, hydrochloric acid, mannitol and water.

(x) 2,2'-dithio-bis-ethane sulfonate, cisplatin, NaCl, phosphoric acid, mannitol, a buffer and water.

(xi) 2,2'-dithio-bis-ethane sulfonate, cisplatin, NaCl, hydrochloric acid, mannitol, a buffer and water.

(xii) 2,2'-dithio-bis-ethane sulfonate, NaCl, hydrochloric acid, and water.

(xiii) 2,2'-dithio-bis-ethane sulfonate, NaCl, phosphoric acid, and water.

(xiv) 2,2'-dithio-bis-ethane sulfonate, NaCl, a buffer, phosphoric acid and water.

(xv) 2,2'-dithio-bis-ethane sulfonate, cisplatin, NaCl, a buffer, hydrochloric acid, and water.

Compositions of Lyophilized Compositions Containing 2,2'-Dithio-Bis-Ethane Sulfonate as the Key Ingredient of the Instant Invention:

This invention is also useful because lyophilized 2,2'-dithio-bis-ethane sulfonate with or without cisplatin would be a method of choice because of the extended shelf life of the lyophilized composition. Additionally, a lyophilized composition is less expensive to manufacture than its aqueous counterpart. When needed for patient administration, the lyophilized drug composition is reconstituted with an aqueous diluent to yield specific concentrations of 2,2'-dithio-bis-ethane sulfonate alone or 2,2'-dithio-bis-ethane sulfonate with cisplatin and chloride salts in the final solution. Reconstitution of lyophilized compositions of 2,2'-dithio-bis-ethane sulfonate with or without cisplatin can be achieved by many types of aqueous solutions including, without restriction, 0.9% NaCl USP, Sterile Water for Injection USP, Dextrose 5% and Water for Injection USP, and the like. The inventors have determined that the disulfide linkage contained within 2,2'-dithio-bis-ethane sulfonate is stable in a variety of aqueous environments (pure water or saline solutions) over a broad pH range, from pH 1.5 to 9.0. One preferred embodiment is a pH of 2,2'-dithio-bis-ethane sulfonate ranging from 4 to 9. The reconstituted solution can be passed through a 0.2 micron filter to avoid micro aggregates of the drug product.

This invention teaches novel lyophilized compositions containing a water soluble disulfide, 2,2'-dithio-bis-ethane sulfonate as a key ingredient, wherein the presence of the disulfide and the parenteral administration of the formulation reduces the risk of cisplatin induced nephrotoxicity, myelosuppression, and neurotoxicity and also potentiates the antitumor activity of cisplatin when treating human patients with cancer.

Lyophilized compositions containing 2,2'-dithio-bis-ethane sulfonate as the key ingredient of the instant invention can be comprised of:

(i) 2,2'-dithio-bis-ethane sulfonate.

(ii) 2,2'-dithio-bis-ethane sulfonate sodium salt.

(iii) 2,2'-dithio-bis-ethane sulfonate, cisplatin and NaCl.

(iv) 2,2'-dithio-bis-ethane sulfonate, cisplatin, NaCl and phosphoric acid.

(v) 2,2'-dithio-bis-ethane sulfonate, cisplatin, mannitol and NaCl.

(vi) 2,2'-dithio-bis-ethane sulfonate, cisplatin, mannitol, NaCl and phosphoric acid.

(vii) 2,2'-dithio-bis-ethane sulfonate and mannitol.

(viii) 2,2'-dithio-bis-ethane sulfonate, mannitol and phosphoric acid.

(ix) 2,2'-dithio-bis-ethane sulfonate, NaCl and phosphoric acid.

(x) 2,2'-dithio-bis-ethane sulfonate, mannitol and hydrochloric acid.

(xi) 2,2'-dithio-bis-ethane sulfonate, NaCl, mannitol and hydrochloric acid.

For this invention the 2,2'-dithio-bis-ethane sulfonate alone or in combination with cisplatin and the other ingredients may be lyophilized and reconstituted before administration. For the purposes of this invention "lyophilized", lyophilize", "freeze-dried", "cryodessicated" all are terms of art which involve the extraction of water from the drug preparation by evaporation of water from the product. For the purposes of this invention the terms "reconstitute", "reconstituted", or "reconstitutable" are used interchangeably and mean to add a pharmaceutically acceptable aqueous diluent to the lyophilized composition to result in an aqueous composition that can be administered to a human patient with cancer.

Another object of this invention is the administration of said lyophilized compositions containing 2,2'-dithio-bis-ethane sulfonate with or without cisplatin and chloride salts, acid or buffer, wherein said compositions are used to reduce the risk of cisplatin induced nephrotoxicity when treating human patients with cancer.

Oral Compositions Containing 2,2'-Dithio-Bis-Ethane-Sulfonate

Oral compositions of 2,2'-dithio-bis-ethane sulfonate or pharmaceutically acceptable salts of 2,2'-dithio-bis-ethane sulfonate can be administered orally to human subjects with cancer who are receiving cisplatin therapy. Solid dosage forms for oral administration include capsules, tablets, pills, powders and granules. In such solid dosage forms, 2,2'-dithio-bis-ethane sulfonate or a pharmaceutically acceptable salt of 2,2'-dithio-bis-ethane sulfonate is admixed with at least one inert customary excipient (or carrier) such as sodium citrate or dicalcium phosphate or (i) fillers or extenders, as for example, starches, lactose, sucrose, glucose, mannitol and silicic acid, (ii) binders, as for example, carboxymethylcellulose, alginates, gelatin, polyvinylpyrrolidinone, sucrose and acacia, (iii) humectants, as for example, glycerol, (iv) disintegrating agents, as for example, agar-agar, calcium carbonate, potato or tapioca starch, algin acid, certain complex silicates and sodium carbonate, (v) solution retarders, as for example, paraffin, (vi) absorption accelerators, as for example, quaternary ammonium compounds, (vii) wetting agents, as for example, cetyl alcohol and glycerol monostearate, (viii) adsorbents, as for example, kaolin and bentonite, and (ix) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using excipients such as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release 2,2'-dithio-bis-ethane sulfonate or pharmaceutically acceptable salts of 2,2'-dithio-bis-ethane sulfonate in a certain part of the intestinal tract in a delayed manner. Examples of embedding compositions which can be used are polymeric substances and waxes.

The active compounds can also be in microencapsulated form, if appropriate, with one or more of the above-mentioned excipients.

Liquid dosage forms for oral administration include physiologically acceptable emulsions, solutions, suspensions, syrups, and elixirs. In addition to 2,2'-dithio-bis-ethane sulfonate or pharmaceutically acceptable salts of 2,2'-dithio-bis-ethane sulfonate, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, dimethylacetamide, N-methyl pyrrolidinone, oils, in particular, cottonseed oil, groundnut oil, corn germ oil, olive oil, polyoxyethylated castor oil, castor oil and sesame oil, glycerol, tetrahydrofurfuryl alcohol, polyethyleneglycols and fatty acid esters of sorbitan or mixtures of theses substances, and the like.

An aspect of the claimed invention is a composition including 2,2'-dithio-bis-ethane sulfonate, or a pharmaceutically acceptable salt thereof, cis-diammine dichloro platinum, a chloride salt, wherein the salt is sodium chloride, and an acid selected from the group consisting of hydrochloric acid and phosphoric acid, in a unit dosage form in a sealed container, wherein the composition is suitable for administration to a human patient with cancer, wherein the concentration of cis-diammine dichloro platinum is between about 0.1 mg/ml and about 1.0 mg/ml, wherein the concentration of 2,2'-dithio-bis-ethane sulfonate is between 1.0 mg per ml to about 320 mg per ml, wherein the concentration of the chloride salt is between 0.1% and 2.5% by weight of water, and wherein the acid is in an amount sufficient to maintain the pH in the range of 2.0 to 6.0. An embodiment of this aspect is where this composition further contains mannitol in a concentration between about 1.0% to about 2.5% by weight of water. Yet another embodiment is this composition further contains a sufficient amount of buffer selected from the group consisting of sodium acetate and phosphate, alone or in combination, to maintain the pH of the composition in the range of 2.0 to 6.0.

Another aspect of this invention is where the human patient with cancer is untreated or previously treated with an anticancer agent.

Yet another aspect of this invention is where the composition is administered in combination with another anticancer agent to the human patient with cancer.

A further aspect of this invention is a composition including: a) cis-diammine dichloro platinum in a concentration between about 0.1 mg per ml and about 1.0 mg per ml; b) 2,2'-dithio-bis-ethane sulfonate, or a pharmaceutically acceptable salt thereof, in a concentration between about 1.0 mg per ml and about 320 mg per ml; c) a chloride salt, wherein the salt is sodium chloride, at a concentration of 0.1% to 2.5% by weight of water; d) mannitol in a concentration between about 1.0% to about 2.5% by weight of water: and e) acid selected from a group consisting of hydrochloric acid and phosphoric acid, alone or in combination, in a sufficient concentration to maintain the pH in the range of 2.0 to 6.0; all of which are in a unit dosage form in a sealed container, wherein the composition is suitable for administration to the human patient with cancer. An embodiment of this aspect is where the composition further contains a buffer selected from the group consisting of sodium acetate or phosphate, alone or in combination, in a sufficient amount to maintain the pH in the range of 2.0 to 6.0.

Another aspect of this invention is a composition including 2,2'-dithio-bis-ethane sulfonate, or a pharmaceutically acceptable salt thereof, and cis-diammine dichloro platinum, in a unit dosage form in a sealed container, wherein the composition is suitable for administration to a human patient with cancer, wherein the concentration of 2,2'-dithio-bis-ethane sulfonate is between 1.0 mg per ml to about 320 mg per ml and the concentration of cis-diammine dichloro platinum is between about 0.1 mg per ml to about 1.0 mg per ml.

Another aspect of the instant invention is a composition including 2,2'-dithio-bis-ethane sulfonate, or a pharmaceutically acceptable salt thereof, in a concentration between about 1.0 mg per ml and about 320 mg per ml and this composition may further contain a chloride salt, wherein the salt is sodium chloride at a concentration of 0.1% to 2.5% by weight of water.

A further aspect of this invention is the above 2,2'-dithio-bis-ethane sulfonate compositions having a pH in the range of 4.0 to 9.0, wherein the pH range is achieved by adding hydrochloric acid or phosphoric acid.

A further aspect of any of the above compositions wherein the composition is in a unit dosage form in a sealed container, wherein the composition is suitable for parenteral administration to an untreated or previously treated human patient with cancer by the injection or infusion thereof from the container.

Yet another aspect of any of the above compositions wherein the composition is administered in combination with another anticancer agent or agents to a human patient with cancer.

Another aspect of this invention is a lyophilized composition including 2,2'-dithio-bis-ethane sulfonate, or a pharmaceutically acceptable salt thereof, wherein the lyophilized composition is reconstituted for administration preceding, simultaneously with or following the administration of an anticancer agent or agents to a human patient with cancer.

Yet a further aspect of this invention is a lyophilized composition including 2,2'-dithio-bis-ethane sulfonate, or a pharmaceutically acceptable salt thereof, wherein the lyophilized composition is reconstituted to an aqueous parenteral composition prior to administration, with a pharmaceutically acceptable aqueous diluent to yield an aqueous composition, wherein the concentration of composition contains between about 1.0 mg/ml to about 320 mg/ml of 2,2'-dithio-bis-ethane sulfonate.

A further aspect of this invention is where the above compositions are reconstituted with a pharmaceutically acceptable aqueous diluent containing 0.1% NaCl to about 2.5% NaCl by weight of water to yield a concentration of 2,2'-dithio-bis-ethane sulfonate between about 1.0 mg/ml and about 320 mg/ml.

Another aspect of this invention is a one of the above compositions further contains a sufficient amount of buffer selected from the group consisting of sodium acetate and phosphate, or a combination thereof, to maintain the pH between about 4.0 and 9.0.

An additional aspect of this invention is a lyophilized composition including 2,2'-dithio-bis-ethane sulfonate, or a pharmaceutically acceptable salt thereof, and cis-diammine dichloro platinum, wherein the composition is reconstituted for administration to a human patient with cancer.

Yet a further aspect of this invention is a lyophilized composition including cis-diammine dichloro platinum, 2,2'-dithio-bis-ethane sulfonate, or a pharmaceutically acceptable salt thereof, and a chloride salt, wherein the salt is sodium chloride, wherein the composition is reconstituted to an aqueous parenteral composition prior to intravenous administration with a pharmaceutically acceptable aqueous diluent previously acidified to a pH in the range of 2.0 to 6.0 by the addition of sufficient amounts of acid selected from the group consisting of hydrochloric acid and phosphoric acid, to yield a composition containing cis-diammine dichloro platinum in a concentration between about 0.1 mg/ml and about 1.0 mg/ml, wherein the concentration of 2,2'-dithio-bis-ethane sulfonate is between about 1.0 mg/ml and about 320 mg/ml, wherein the concentration of chloride salt is between 0.1% and 2.5% by weight of water, and wherein the acid is in an amount sufficient to maintain the pH in the range of about 2.0 to about 6.0, and wherein the pharmaceutically acceptable diluent is selected from the group consisting of Sterile Water for Injection USP, Dextrose 5% and Water for Injection USP, 0.9% NaCl for Injection USP, Dextrose 5% 0.9% NaCl for Injection USP, and Lactated Ringer's Solution.

An embodiment of this aspect is where the above lyophilized composition further contains a buffer selected from the group consisting of sodium acetate and phosphate.

Another aspect of this invention is a lyophilized composition including 2,2'-dithio-bis-ethane sulfonate, or a pharmaceutically acceptable salt thereof, and a chloride salt, wherein the salt is sodium chloride, wherein the composition is reconstituted to yield a composition for administration to human subjects with cancer, wherein the concentration of 2,2'-dithio-bis-ethane sulfonate is between about 1.0 mg per ml and about 320 mg per ml, wherein the concentration of the chloride salt is between 0.1% and 2.5% by weight of water, and wherein the acid is in an amount sufficient to maintain the pH in the range of about 2.0 to about 6.0.

Further embodiments of this composition contains a buffer selected from the group consisting of sodium acetate and phosphate or mannitol or phosphoric acid.

Another aspect of this invention is a method of administration of 2,2'-dithio-bis-ethane sulfonate or pharmaceutically acceptable salts thereof, wherein aqueous 2,2'-dithio-bis-ethane sulfonate or the salts are parenterally administered preceding, simultaneously with or following the administration of cis-diammine dichloro platinum to a human patient with cancer.

Yet another aspect of this invention is a method of administration of 2,2'-dithio-bis-ethane sulfonate, or pharmaceutically acceptable salts thereof, wherein aqueous 2,2'-dithio-bis-ethane sulfonate or the salts are orally administered preceding, simultaneously with or following the administration of cis-diammine dichloro platinum to a human patient with cancer.

Another aspect of this invention is where pharmaceutically acceptable salt of 2,2'-dithio-bis-ethane sulfonate is selected from the group consisting of (a) disodium 2,2'-dithio-bis-ethane sulfonate, (b) monosodium 2,2'-dithio-bis-ethane sulfonate, (c) sodium potassium 2,2'-dithio-bis-ethane sulfonate, (d) dipotassium 2,2'-dithio-bis-ethane sulfonate, (e) calcium 2,2'-dithio-bis-ethane sulfonate, (f) magnesium 2,2'-dithio-bis-ethane sulfonate and (g) monopotassium 2,2'-dithio-bis-ethane sulfonate.

DETAILED DESCRIPTION OF THE PREFERRED EMBODIMENTS

Figure 1:
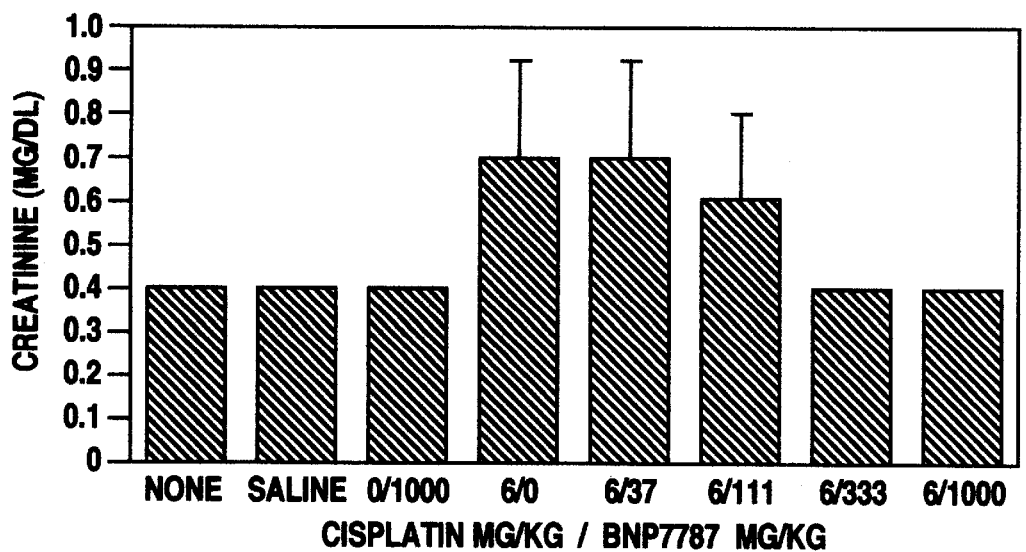
FIG. 1. Serum Creatinine Values on Day 5 Post Treatment with i.v. Cisplatin (6 mg/kg) With or Without Increasing Doses of i.v. 2,2'-Dithio-Bis-Ethane Sulfonate (BNP7787).

In its preferred embodiments, this invention involves the preparation and administration of 2,2'-dithio-bis-ethane sulfonate compositions or formulations preceding, simultaneously with, or following the administration of cis-diammine dichloro platinum.

EXAMPLES

The following examples illustrate selected modes for carrying out the claimed invention and are not meant to be construed as limiting the specification and claims in any way.

Example 1
Preparation of 2.2'-Dithio-Bis-Ethane Sulfonate 2,2'-Dithio-bis-ethane sulfonate was prepared by oxidizing 2-mercapto ethane sulfonate in water with equimolar amount of iodine as previously reported by Lamaire and Reiger (Lemaire and Reiger, *J. Org. Chem.*, 26, 1330–1, 1961).

Example 2
Stability of 2,2'-Dithio-Bis-Ethane Sulfonate

The stability of 2,2'-dithio-bis-ethane sulfonate at room temperature was determined at pH ranges of 1.5 to 9.0. 2,2'-dithio-bis-ethane sulfonate, as synthesized by the method described above, was found to be stable in the pH range of 1.0–11.0.

The stability of 2,2'-dithio-bis-ethane sulfonate in acidic and basic aqueous media can be studied as described in this example. In a typical experiment, 50 mg of 2,2'-dithio-bis-ethane sulfonate (as produced by using the above described method) was dissolved in one ml of water and the pH of the solution adjusted to 1.5, 2.0, 3.0, 4.0, 5.0 and 6.0 by adding 1N hydrochloric acid in water or the pH adjusted to 8.0, 9.0, 10.0 or 11.0 by adding 1N sodium hydroxide in water. The reaction mixture was then stirred for 24 hours at room temperature, the water was removed at reduced pressure, dissolved in spectral grade $D_2O$, and the proton NMR spectrum was recorded. The results demonstrated that only peaks corresponding to the starting material were observed by NMR spectra, and that no additional peaks were observed. These data indicate that 2,2'-dithio-bis-ethane sulfonate was stable in alkaline or acidic aqueous solutions at pH values from 1.5 to 9.0.

The stability of 2,2'-dithio-bis-ethane sulfonate at pH 1.5 is further studied by heating the reaction mixture to 100 degrees Celsius for 10 minutes. No change in the proton spectrum was observed by heating the 2,2'-dithio-bis-ethane sulfonate (pH 1.5). These data indicate that 2,2'-dithio-bis-ethane sulfonate was stable in alkaline or acidic aqueous solutions at pH values from 1.5 to 9.0.

Example 3
Method #1 to Produce a Formulation Containing Cisplatin and 2.2'-Dithio-Bis-Ethane Sulfonate This example was designed to detail one method to produce a formulation containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. USP grade of sodium chloride (NaCl; purchased from VWR Scientific) is dissolved in sterile, injectable water to a final concentration of 0.9% NaCl by weight of water. A suitable amount of pure hydrochloric acid (HCl, 99.999%; purchased from Aldrich Chemical Company) is added to the sterile, injectable 0.9% sodium chloride solution in order to obtain a final pH in the range of approximately 2.0 to 6.0.

Step 2. One part by weight of pure, cisplatin (99.999%, purchased from Aldrich Chemical Company) is added to the admixture of Step 1. The cisplatin is allowed to completely dissolve by agitation (1500–2500 rpm) at room temperature, for approximately 60 to 90 minutes in the dark.

Step 3. Then, 15 parts by weight of disodium 2,2'-dithio-bis-ethane sulfonate (as produced above in Example 1) is added the mixture of Step 2. This mixture is agitated until complete dissolution and the final pH is adjusted to a pH ranging between approximately pH 2.0 and pH 6.0 by adding pure hydrochloric acid (99.999%, purchased from Aldrich Chemical Company).

Step 4. The solution of Step 3 is sterilized via filtration through a sterile 0.2 micron filter (obtained from VWR Scientific).

Step 5. The formulation of Step 4 is stored in sterile injection vials wherein each vial contains approximately 0.9 mg of cisplatin and 14.3 mg of 2,2'-dithio-bis-ethane sulfonate per ml of solution.

Example 4
Method #2 to Produce a Formulation Containing Cisplatin and 2.2'-Dithio-Bis-Ethane Sulfonate This example was designed to detail another method to produce a formulation containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. USP grade of sodium chloride (NaCl; purchased from VWR Scientific) is dissolved in sterile, injectable water to a final concentration of 0.9% NaCl by weight of water.

Step 2. Disodium 2,2'-dithio-bis-ethane sulfonate (as produced above in Example 1; fifteen mg per milliliter of solution is added to the sterile, injectable 0.9% NaCl solution from Step 1. The 2,2'-dithio-bis-ethane sulfonate is allowed to completely dissolve by agitation (1500–2500 rpm) at room temperature. Complete dissolution requires approximately 5–10 minutes at room temperature. The pH of the 2,2'-dithio-bis-ethane sulfonate solution is adjusted to a pH ranging between approximately pH 2.0 and pH 6.0 by adding pure (99.999% purity) hydrochloric acid.

Step 3. Pure (99.999% purity) cisplatin is added (1 part by weight) to the solution of Step 2. This mixture is agitated until complete dissolution and the final pH is adjusted to a pH ranging between approximately pH 2.0 and pH 6.0 by adding pure (99.999% purity) hydrochloric acid.

Step 4. The solution of Step 3 is sterilized via filtration through a sterile 0.2 micron filter (obtained from VWR Scientific).

Step 5. The formulation of Step 4 is stored in sterile injection vials wherein each vial contains approximately 0.9 mg of cisplatin and 14.3 mg of 2,2'-dithio-bis-ethane sulfonate per ml of formulation.

Example 5
Method #3 to Produce a Formulation Containing Cisplatin and 2.2'-Dithio-Bis-Ethane Sulfonate This example was designed to detail another method to produce a formulation containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. A suitable amount of pure, disodium 2,2'-dithio-bis-ethane sulfonate (as produced in Example 1) is dissolved in sterile, injectable water to a concentration of 15.0 mg/ml.

Step 2. USP grade sodium chloride crystals (NaCl; purchased from VWR Scientific) is added to the solution of Step 1 such that the final concentration of NaCl is 0.9% by weight of water.

Step 3. The pH of the 2,2'-dithio-bis-ethane sulfonate—NaCl solution of Step 2 is adjusted to range between approximately pH 2.0 and pH 6.0 by the addition of pure (99.999% purity), hydrochloric acid (purchased from Aldrich Chemical Company).

Step 4. An amount of pure (99.999% purity) cisplatin is added to the solution of Step 3 such that the final concentration is approximately 1.0 mg/ml cisplatin and the solution is agitated until complete dissolution of the cisplatin is achieved. The dissolution of cisplatin in the solution is carried out in the dark.

Step 5. The solution of Step 4 is sterilized via filtration through a sterile 0.2 micron filter.

Step 6. The formulation of Step 5 is store in sterile injection vials wherein each vial contains approximately 1.0 mg of cisplatin and 14.3 mg of 2,2'-dithio-bis-ethane sulfonate per ml of injection solution.

Example 6
Method #4 to Produce a Formulation Containing Cisplatin and 2.2'-Dithio-Bis-Ethane Sulfonate This example was designed to detail another method to produce a formulation containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. USP grade sodium chloride (NaCl; purchased from VWR Scientific) dissolved in sterile, injectable water to a final concentration of 0.9% NaCl by weight of water.

Step 2. The pH of this NaCl solution is brought to approximately 2.0 to 6.0 by the addition of 99.999% pure hydrochloric acid (purchased from Aldrich Chemical Company).

Step 3. Pure (99.999% purity) cisplatin (obtained from Aldrich Chemical Company) is added in 0.5 mg to each milliliter of the solution obtained in Step 2 and allowed to dissolve completely by agitation (1500–2500 rpm) for approximately 60 to 90 minutes at room temperature in the dark.

Step 4. Then, 30 milligrams of disodium 2,2'-dithio-bis-ethane sulfonate (as produced in Example 1) is added to each milliliter of the solution Step 3. The 2,2'-dithio-bis-ethane sulfonate—cisplatin mixture is allowed to completely dissolve with agitation at room temperature.

Step 5. The pH of the disodium 2,2'-dithio-bis-ethane sulfonate—cisplatin solution is adjusted to a final pH ranging between approximately 2.0 and 6.0 by the addition of pure (99.999% purity) hydrochloric acid (obtained from Aldrich Chemical Company).

Step 6. The solution of Step 5 is sterilized via filtration through a sterile 0.2 micron filter (obtained from VWR Scientific).

Step 7. The formulation of Step 6 is stored in sterile injection vials wherein each vial contains 0.5 mg of cisplatin and 30.0 mg of disodium 2,2'-dithio-bis-ethane sulfonate per ml of injection solution.

Example 7
Method #5 to Produce a Formulation Containing Cisplatin and 2.2'-Dithio-Bis-Ethane Sulfonate This example was designed to detail another method to produce a formulation containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. USP grade sodium chloride (NaCl; purchased from VWR Scientific) dissolved in sterile, injectable water to a final concentration of 0.9% NaCl by weight of water.

Step 2. An amount of pure (99.999% purity) hydrochloric acid (obtained from Aldrich Chemical Company) is added to the NaCl solution of Step 1 in order to obtain a final pH in the range of approximately 2.0 to 6.0.

Step 3. An amount of USP grade potassium chloride crystals (KCl; purchased from VWR Scientific) is dissolved in the solution of Step 2 (0.9% NaCl) such that the final concentration of potassium chloride is 0.1% by weight.

Step 4. One milligram of pure (99.999% purity) cisplatin is added to each milliliter of the solution of Step 3 and is completely dissolved by agitation (1500 to 2500 rpm) for approximately 60 to 90 minutes at room temperature in the dark.

Step 30 milligrams of disodium 2,2'-dithio-bis-ethane sulfonate (as produced by Example 1) is added to each milliliter the solution of Step 4. This mixture is agitated until complete dissolution and the final pH ranging between approximately pH 2.0 and pH 6.0 by adding pure (99.999% purity) hydrochloric acid (purchased from Aldrich Chemical Company).

Step 6. The solution of Step 5 is sterilized via filtration through a sterile 0.2 micron filter (obtained from VWR Scientific).

Step 7. The formulation of Step 6 is stored in sterile injection vials wherein each vial contains approximately 1.0 mg of cisplatin and 30.0 mg of disodium 2,2'-dithio-bis-ethane sulfonate per ml of solution.

Example 8
Method #6 to Produce a Formulation Containing Cisplatin and 2.2'-Dithio-Bis-Ethane Sulfonate This example was designed to detail another method to produce a formulation containing cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. USP grade sodium chloride (NaCl; purchased from VWR Scientific) dissolved in sterile, injectable water to a final concentration of 0.9% NaCl by weight of water. A suitable amount of pure (99.999% purity) hydrochloric acid is added to the sterile, injectable 0.9% sodium chloride solution in order to obtain a final pH in the range of approximately 2.0 to 6.0.

Step 2. Pure mannitol (99+% purity, purchased from Aldrich Chemical Company) is dissolved in the solution of Step 1 so that the concentration of mannitol in said solution is 1.0% by weight of the solution.

Step 2. One milligram of pure, cisplatin (purchased from Aldrich Chemical Company, grade 99.999% purity) is added to each milliliter of the solution of Step 2. The cisplatin is allowed to completely dissolve by agitation (1500–2500 rpm) at room temperature. This should take approximately 60 to 90 minutes at room temperature in the dark.

Step 4. Then, 30 mg of disodium 2,2'-dithio-bis-ethane sulfonate (as produced in Example 1) is added to each milliliter of the solution of Step 3. This solution is agitated until complete dissolution of 2,2'-dithio-bis-ethane sulfonate is achieved and the final pH is adjusted to a pH ranging between approximately pH 2.0 and pH 6.0 by adding pure (99.999% purity) hydrochloric acid (purchased from Aldrich Chemical Company).

Step 5. The solution of Step 4 is sterilized via filtration through a sterile 0.2 micron filter.

Step 6. The formulation of Step 5 is stored in sterile injection vials wherein each vial contains approximately 1.0 mg of cisplatin and 30.0 mg of disodium 2,2'-dithio-bis-ethane sulfonate per ml of injection solution.

Example 9
Stability of 2,2'-Dithio-Bis-Ethane Sulfonate and Cisplatin Formulations This example was designed to study the stability of 2,2'-dithio-bis-ethane sulfonate and cisplatin formulations.

1. First, 2,2'-dithio-bis-ethane sulfonate—cisplatin formulations were prepared according to Examples 3 through 8.

2. The final pH of each formulation was adjusted to a range of 2.0 to 6.0.

3. Each pH adjusted 2,2'-dithio-bis-ethane sulfonate—cisplatin formulation was stored in a sealed glass vial protected from fluorescent light at room temperature (approximately 27 plus or minus 2 degrees Celsius).

4. The stability of each pH adjusted 2,2'-dithio-bis-ethane sulfonate—cisplatin formulation was analyzed on a weekly basis for at least 6 (six) months by nuclear magnetic resonance (NMR) or HPLC analysis. The NMR spectra or HPLC analysis was compared to a freshly prepared and pH adjusted 2,2'-dithio-bis-ethane sulfonate—cisplatin formulation. The similarity of NMR spectra or HPLC retention times and peaks corresponding to the freshly prepared formulation denotes stability of the pH adjusted formulation over time.

Example 10
Method to Produce a Parenteral Solution Containing Cisplatin and 2.2'-Dithio-Bis-Ethane Sulfonate from a Lyophilized Formulation of Cisplatin and 2.2'-Dithio-Bis-Ethane Sulfonate This example was designed to detail one method to produce a formulation containing cisplatin and disodium 2,2'-dithio-bis-ethane sulfonate by reconstitution of a lyophilized formulation of cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus or minus 1%.

Step 1. USP grade of sodium chloride (NaCl; purchased from VWR Scientific) is dissolved in sterile, injectable water to a final concentration of 0.9% NaCl by weight of water. A suitable amount of pure hydrochloric acid (HCl, 99.999%; purchased from Aldrich Chemical Company) is added to the sterile, injectable 0.9% sodium chloride solution in order to obtain a final pH in the range of approximately 2.0 to 6.0.

Step 2. One part by weight of pure, cisplatin (99.999%, purchased from Aldrich Chemical Company) is added to the admixture of Step 1. The cisplatin is allowed to completely dissolve by agitation (1500–2500 rpm) at room temperature, for approximately 60 to 90 minutes in the dark.

Step 3. Then, 15 parts by weight of disodium 2,2'-dithio-bis-ethane sulfonate (as produced above in Example 1) is added the mixture of Step 2. This mixture is agitated until complete dissolution and the final pH is adjusted to a pH ranging between approximately pH 2.0 and pH 6.0 by adding pure hydrochloric acid (99.999%, purchased from Aldrich Chemical Company).

Step 4. The acidified NaCl solution containing cisplatin and 2,2'-dithio-bis-ethane sulfonate from step 3 is then lyophilized using a commercially available equipment. The lyophilized drug formulation can be stored at room temperature in amber vials which are shielded from light for 6 months to one year until needed for patient administration.

Step 5. When needed for patient administration, the lyophilized drug formulation Step 4 is reconstituted to yield a cisplatin concentration of 0.9 mg per milliliter and a concentration of 2,2'-dithio-bis-ethane sulfonate of 14.3 mg per milliliter by using Sterile Water USP for Injection which has been acidified to a pH of 2.0 to 6.0 by using a sufficient quantity of pure hydrochloric acid or phosphoric acid. This reconstituted aqueous formulation is passed through a sterile 0.2 micron filter and can be administered to the patient.

Example 11
Method to Produce a Parenteral Solution Containing Cisplatin and 2,2'-Dithio-Bis-Ethane Sulfonate from a Lyophilized Formulation of Cisplatin and 2,2'-Dithio-Bis-Ethane Sulfonate This example was designed to detail one method to produce a formulation containing cisplatin and disodium 2,2'-dithio-bis-ethane sulfonate by reconstitution of a lyophilized formulation of cisplatin and disodium 2,2'-dithio-bis-ethane sulfonate. For the purpose of this example, cisplatin and cis-diammine dichloro platinum are used interchangeably. For the purpose of this example, "approximately" is defined to include a range of plus minus 1%.

Step 1. USP grade of sodium chloride (NaCl; purchased from VWR Scientific) is dissolved in sterile, injectable water to a final concentration of 0.9% NaCl by weight of water. A suitable amount of pure phosphoric acid (H3PO4, 99.999%; purchased from Aldrich Chemical Company) is added to the sterile, injectable 0.9% sodium chloride solution in order to obtain a final pH in the range of approximately 2.0 to 6.0.

Step 2. One milligram of pure, cisplatin (99.999%, purchased from Aldrich Chemical Company) is added to each milliliter of the solution of Step 1. The cisplatin is allowed to completely dissolve by agitation (1500–2500 rpm) at room temperature, for approximately 60 to 90 minutes in the dark.

Step 3. Then, 15 milligrams of disodium 2,2'-dithio-bis-ethane sulfonate (as produced above in Example 1) is added to each milliliter of the solution of Step 2. This solution is agitated until complete dissolution and the final pH is adjusted to a pH ranging between approximately pH 2.0 and pH 6.0 by adding pure hydrochloric acid (99.999%, purchased from Aldrich Chemical Company).

Step 4. The acidified NaCl solution containing cisplatin and 2,2'-dithno-bis-ethane sulfonate from step 3 is then lyophilized using a commercially available equipment. The lyophilized drug formulation can be stored at room temperature in amber vials which are shielded from light for 6 months to one year until needed for patient administration.

Step 5. When needed for patient administration, the lyophilzed drug formulation Step 4 is reconstituted to yield a cisplatin concentration of approximately 1.0 mg per milliliter and a concentration of 2,2'-dithio-bis-ethane sulfonate of 15.0 mg per milliliter by using Sterile Water USP for Injection. This reconstituted aqueous formulation is passed through a sterile 0.2 micron filter (obtained from VWR Scientific) and can be administered to the patient.

Example 12

Method to Produce a Parenteral Solution Containing 2,2'-Dithio-Bis-Ethane Sulfonate from a Lyophilized Formulation of 2,2'-Dithio-Bis-Ethane Sulfonate This example was designed to detail one method to produce a formulation containing disodium 2,2-dithio-bis-ethane sulfonate for the purpose of administering said solution during human cancer therapy with cis-diammine dichloro platinum by reconstitution of a lyophilized formulation of disodium 2,2'-dithio-bis-ethane sulfonate. For the purpose of this example, "approximately" is defined to include a range of plus or minus 1%.

Step 1. USP grade of sodium chloride (NaCl; purchased from VWR Scientific) is dissolved in Sterile Water for Injection USP to a final concentration of 0.9% NaCl by weight of water. Alternatively Sterile 0.9% NaCl Solution for Injection may be used for Step 1.

Step 2. Then, 15 milligrams of disodium 2,2'-dithio-bis-ethane sulfonate (as produced above in Step 1) is added to each milliliter of the solution in Step 1. This mixture is agitated until complete dissolution of the 2,2'-dithio-bis-ethane sulfonate is observed (30 to 60 minutes).

Step 3. The 0.9% NaCl solution containing dissolved 2,2'-dithio-bis-ethane sulfonate from Step 2 is then lyophilized using a commercially available equipment. The lyophilized drug formulation containing 2,2'-dithio-bis-ethane sulfonate can be stored at room temperature in amber vials which are shielded from light for 6 months to one year until needed for patient administration.

Step 4. When needed for patient administration, the lyophilized 2,2'-dithio-bis-ethane sulfonate drug formulation from Step 3 is reconstituted to yield a concentration of 2,2'-dithio-bis-ethane sulfonate of 15.0 mg per milliliter by using Sterile Water USP for Injection. This reconstituted aqueous 2,2'-dithio-bis-ethane sulfonate formulation is passed through a sterile 0.2 micron filter (obtained from VWR Scientific) and can be administered to the patient.

Example 13

Method to Produce An Aqueous Parenteral Solution Containing 2,2'-Dithio-Bis-Ethane Sulfonate This example was designed to detail one method to produce a formulation containing disodium 2,2'-dithio-bis-ethane sulfonate for the purpose of administering said solution during human cancer therapy with cis-diammine dichloro platinum. For the purpose of this example, "approximately" is defined to include a range of plus or minus 1%.

Step 1. USP grade of sodium chloride (NaCl; purchased from VWR Scientific) is dissolved in Sterile Water for Injection USP to a final concentration of 0.9% NaCl by weight of water. Alternatively Sterile 0.9% NaCl Solution for Injection may be used for Step 1.

Step 2. Then, 15 mg of disodium 2,2'-dithio-bis-ethane sulfonate (as produced above in Step 1) is added to each milliliter of the solution in Step 1. This mixture is agitated until complete dissolution of the 2,2'-dithio-bis-ethane sulfonate is observed (30 to 60 minutes). The final concentration of disodium 2,2'-dithio-bis-ethane sulfonate is 15 mg/ml.

Step 3. When needed for patient administration, the solution containing 2,2'-dithio-bis-ethane sulfonate drug formulation from Step 2 is can be administered to the patient.

Example 14

Figure 2:
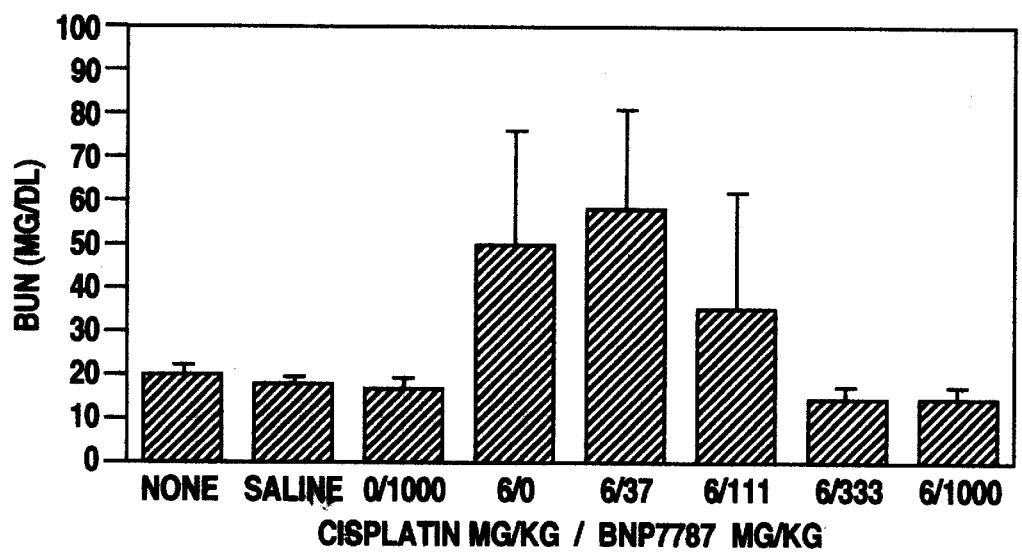
FIG. 2. Serum BUN (Blood Urea Nitrogen) Values on Day 5 Post Treatment with i.v. Cisplatin (6 mg/kg) With or Without Increasing Doses of i.v. 2,2'-Dithio-Bis-Ethane Sulfonate (BNP7787).
Figure 3:
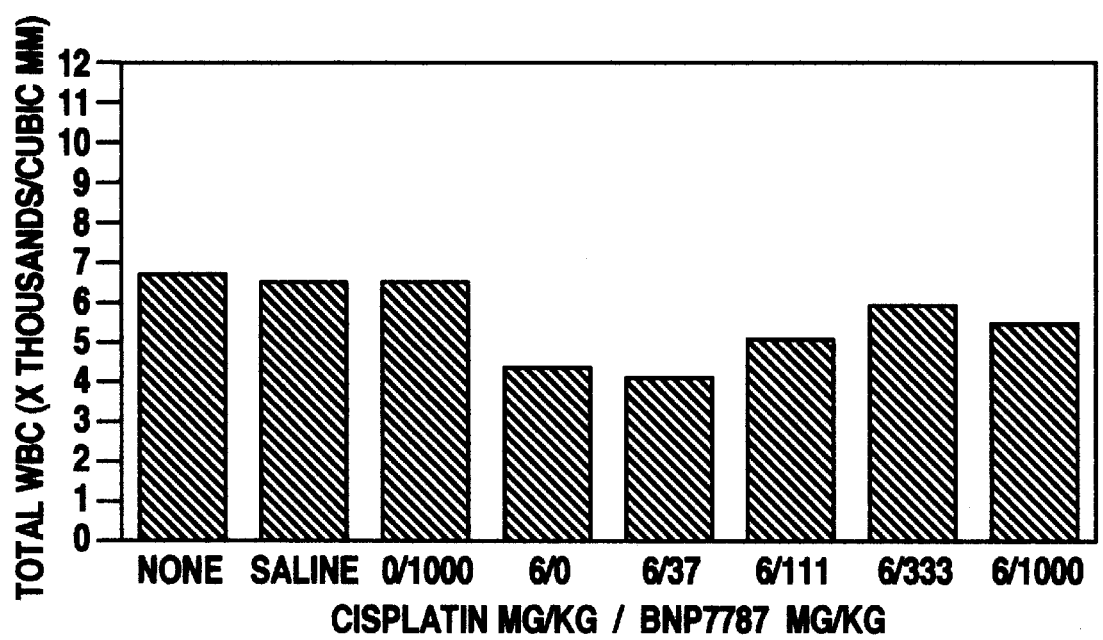
FIG. 3. Total WBC Values on Day 5 Post Treatment with i.v. Cisplatin (6 mg/kg) With or Without Increasing Doses of i.v. 2,2'-Dithio-Bis-Ethane Sulfonate (BNP7787).

In Vivo Demonstration of Protection by 2,2'-Dithio-Bis-Ethane Sulfonate (BNP7787) Against Cisplatin Induced Nephrotoxicity and Myelosuppression in Fischer Rats: Use of Concurrently Administered 2,2'-Dithio-Bis-Ethane Sulfonate and Cisplatin by Parenteral Injection This Example was designed to demonstrate the in vivo protective effects of 2,2'-dithio-bis-ethane sulfonate (also referred to as BNP7787) administered at 1,000 mg/kg by a single i.v. injection in Fischer rats (150–200 g) receiving a nephrotoxic dose of cisplatin (6 mg/kg i.v. single injection) when the two drugs are administered substantially contemporaneously (cisplatin and 2,2'-dithio-bis-ethane sulfonate given concurrently). The data from these studies are shown below in FIGS. 1 and 2. Under Good Laboratory Practice (GLP) conditions, Fischer rats (10 rats per treatment group) were treated with or without escalating doses of BNP7787 (up to 1000 mg/kg) administered by i.v. injection with a nephrotoxic dose of cisplatin (6 mg/kg). Serum BUN (FIG. 2) and Creatinine (FIG. 1) values were measured on day 5 and the animals were weighed daily. As shown in FIGS. 1 and 2, BNP7787 demonstrates a significant (100% renal protection at 333 and 1000 mg/kg of BNP7787) renal protective effect as assessed by day 5 Creatinine (FIG. 1) and BUN (FIG. 2) values compared to cisplatin treated controls. At the 37 mg/kg dose of BNP7787, a slight increase in nephrotoxicity (as measured by plasma BUN and creatinine levels and by histopathology) relative to cisplatin only treated groups was observed (FIG. 2). FIG. 3 demonstrates a dose-dependent protective effect of 2,2'-dithio-bis-ethane sulfonate against cisplatin induced myelosuppression as measured by mean plasma White Blood Counts (WBC). The mean day 5 WBC levels of rats treated with higher doses of 2,2'-dithio-bis-ethane sulfonate, namely the 333 mg/kg and 1,000 mg/kg treatment groups, are approximately 6,800 and 6,200, respectively. These mean WBC values are within 15% of the WBC values for untreated controls. The day 5 mean WBC counts for the cisplatin only and low dose (37 mg/kg) 2,2'-dithio-bis-ethane sulfonate treatment groups are approximately 4,800 and 4,500, respectively and represent a 32% to 36% reduction in the day 5 mean WBC from the untreated control group. The Fischer rat model is highly correlated with cisplatin induced nephrotoxicity in humans and is thus an excellent animal model to support the utility of 2,2'-dithio-bis-ethane sulfonate to protect against cisplatin induced nephrotoxicity in humans. This study documents several aspects of the invention: (1) evidences a clear dose-response effect of 2,2'-dithio-bis-ethane sulfonate in providing renal protection from cisplatin induced nephrotoxicity, (2) evidences the ability of 2,2'-dithio-bis-ethane sulfonate to provide 100% renal protection from a highly nephrotoxic dose of cisplatin, and (3) evidences a dose dependent protective effect of 2,2'-dithio-bis-ethane sulfonate against cisplatin induced myelosuppression.

Example 15
Potentiation of Cisplatin Antitumor Activity by Parenteral Administration of BNP7787 (2,2'-dithio-bis-ethane sulfonate)

Figure 4:
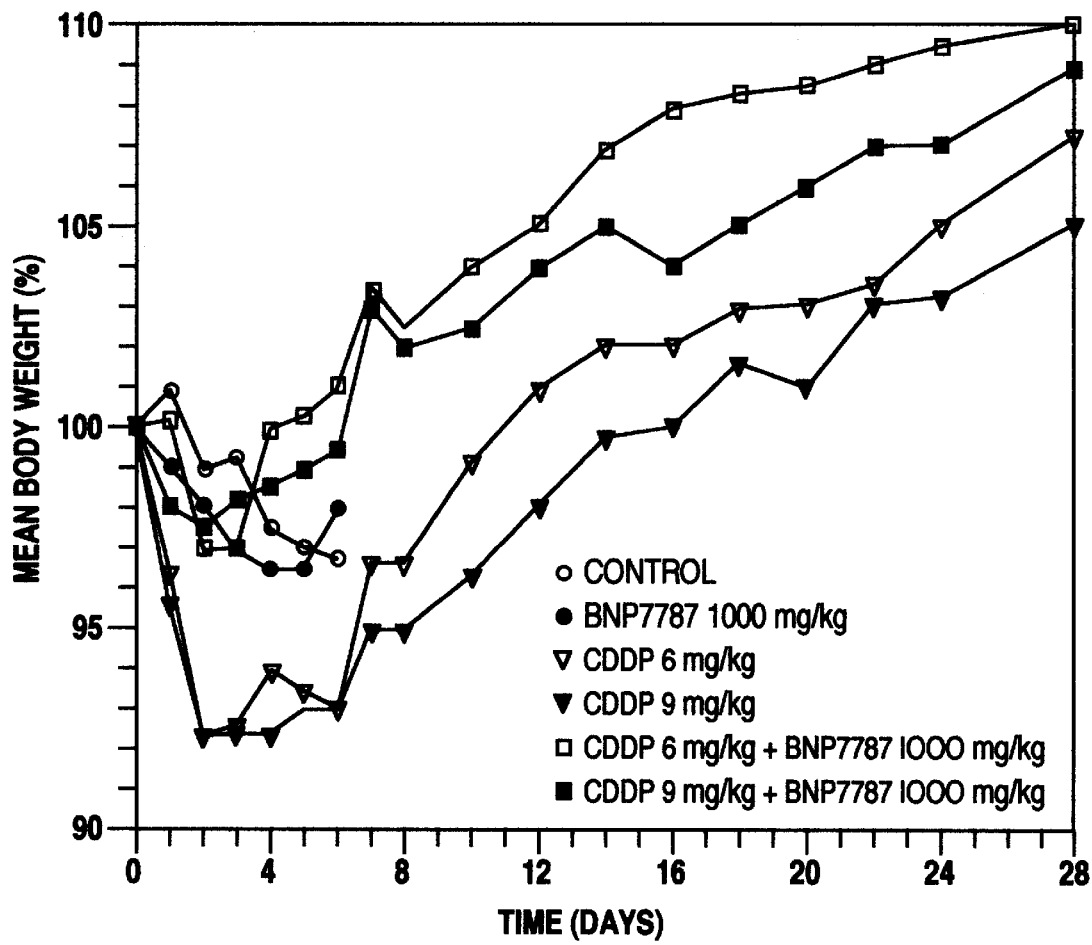
FIG. 4. Weight Change in Tumor Bearing Fischer Rats Treated with Parenteral Cisplatin (6 mg/kg or 9 mg/kg) and 2,2'-Dithio-Bis-Ethane Sulfonate (BNP7787 @ 1,000 mg/kg).
Figure 5:
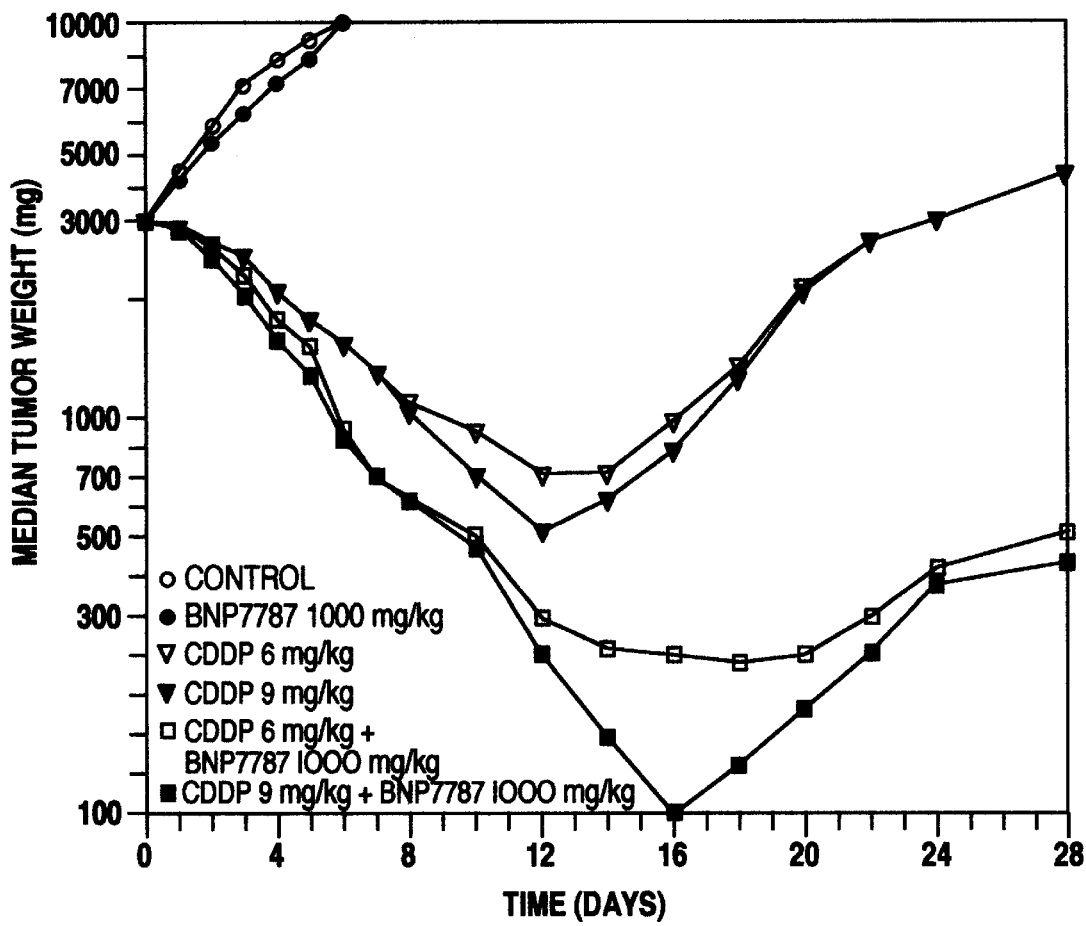
FIG. 5. Antitumor Response of Tumor Bearing Fischer Rats Treated with Parenteral Cisplatin (6 mg/kg or 9 mg/kg) and 2,2'-Dithio-Bis-Ethane Sulfonate (BNP7787 @ 1000 mg/kg).

The antitumor activity and toxicity, as measured by weight changes estimated by changes in tumor volumes and animal weights, respectively, of escalating doses of parenterally (intravenously) administered cisplatin (6 mg/kg and 9 mg/kg) with or without substantially contemporaneously intravenously administered BNP7787 (1000 mg/kg) was investigated in Fischer rats bearing subcutaneous established (~3.0 g) WARD colon cancer. In the untreated control rats, it should be noted that the subcutaneous 3.0 gram WARD colon carcinoma tumors will grow from 3.0 grams to about 10 grams in size in about 7 days (shown in FIG. 5). In FIG. 4, the data show that untreated tumor bearing rats and rats treated with BNP7787 only lose about 2 to 4% of their body weight in about 6 days (open and closed circles, respectively). It is notable that rats treated with cisplatin alone (6 mg/kg and 9 mg/kg) lose up to 8% of their body weight at 6 days. Treatment with i.v. BNP7787 (1000 mg/kg) at both dose levels of cisplatin (6 mg/kg and 9 mg/kg) were clearly protective against renal damage as measured by weight loss, and the rats in these groups receiving cisplatin and BNP7787 demonstrated greater mean weights than all other treatment groups (compare open and closed squares to open and closed triangles). This observation suggests that treatment with BNP7787 may prevent or reduce other cisplatin toxicities, including neurotoxicity and emesis, leading to weight loss in rats. Another important observation is that the cisplatin/BNP7787 treated groups had potentiation of cisplatin antitumor activity for both the 6 mg/kg and 9 mg/kg dose groups (FIG. 5-open and closed squares, respectively). Rats treated with cisplatin only at doses of 6 mg/kg and 9 mg/kg had a maximum reduction in median tumor weight from 3,000 mg to 700 and 500 mg, respectively. Rats treated with cisplatin at doses of 6 mg/kg and 9 mg/kg immediately followed by ad seriatim administration of BNP7787 using a single i.v. dose of 1,000 mg/kg had a maximum reduction in median tumor weight from 3,000 mg to less than 300 and 100 mg, respectively. This data in FIG. 5 evidences several important features of 2,2'-dithio-bis-ethane sulfonate when it is used substantially contemporaneously with cisplatin: (1) 2,2'-dithio-bis-ethane sulfonate lacks intrinsic antitumor activity, (2) substantially contemporaneously administered 2,2'-dithio-bis-ethane sulfonate does not abrogate the antitumor activity of cisplatin, (3) substantially contemporaneous administration of 2,2'-dithio-bis-ethane sulfonate appears to potentiate the antitumor activity of cisplatin and (4) these data demonstrate the significant antitumor potentiation of cisplatin antitumor activity is mediated and enhanced by 2,2'-dithio-bis-ethane sulfonate.

Example 16
Stability of 2,2'-dithio-bis-ethane sulfonate At pH Ranging From 1.5 to 9

A control solution of the disodium salt of 2,2'-dithio-bis-ethane sulfonate was prepared by dissolving 9 mg of sodium chloride (USP grade) and 30 mg of the disodium salt of 2,2'-dithio-bis-ethane sulfonate in 1 ml of deuterated water (99.999%). The pH of the control was adjusted to 7.0 using 1N DC1. This deuterated solution was directly used as the control for the NMR sample.

Preparation of the assay solutions containing 2,2'-dithio-bis-ethane sulfonate were also made in a similar manner, 30 mg of the disodium salt of 2,2'-dithio-bis-ethane sulfonate was added to each vial containing 1 ml of 0.9% sodium chloride in deuterated water and agitated to dissolve completely. The homogenous solution obtained was then adjusted to the desired pH using either 1N DC1 or 1N deuterated sodium hydroxide solution. The pH adjusted aqueous solutions were then analyzed by high field NMR (300 MHz, Bruker) for a period of 48 hours at three hour intervals. The stability of the disodium salt of 2,2'-dithio-bis-ethane sulfonate in aqueous solution at pH 1.5 was also determined at elevated temperature by heating the aqueous solution at 100° C. for 15 minutes.

$^1$H-NMR spectra of the monosodium salt of 2-mercapto ethane sulfonate sodium (mesna), and the disodium salt of 2,2'-dithio-bis-ethane sulfonate provided two sets of distinctive peaks whereby molecular interconversions or degradation could be monitored. The proton NMR spectrum of mesna provided multiplets at 2.88$\delta$ and 3.19$\delta$ whereas the disodium salt of 2,2'-dithio-bis-ethane sulfonate compound had characteristic multiplet signals at 3.09$\delta$.

Example 17
Oral Formulations Containing 2,2'-Dithio-Bis-Ethane-Sulfonate

Oral formulations of 2,2'-dithio-bis-ethane sulfonate or pharmaceutically acceptable salts of 2,2'-dithio-bis-ethane sulfonate can be administered orally to human subjects with cancer who are receiving cisplatin therapy. Solid dosage forms for oral administration include capsules, tablets, pills, powders and granules. In such solid dosage forms, 2,2'-dithio-bis-ethane sulfonate or a pharmaceutically acceptable salt of 2,2'-dithio-bis-ethane sulfonate is admixed with at least one inert customary excipient (or carrier) such as sodium citrate or dicalcium phosphate or (i) fillers or extenders, as for example, starches, lactose, sucrose, glucose, mannitol and silicic acid, (ii) binders, as for example, carboxymethylcellulose, alginates, gelatin, polyvinylpyrrolidinone, sucrose and acacia, (iii) humectants, as for example, glycerol, (iv) disintegrating agents, as for example, agar-agar, calcium carbonate, potato or tapioca starch, align acid, certain complex silicates and sodium carbonate, (v) solution retarders, as for example, paraffin, (vi) absorption accelerators, as for example, quaternary ammonium compounds, (vii) wetting agents, as for example, cetyl alcohol and glycerol monostearate, (viii) adsorbents, as for example, kaolin and bentonite, and (ix) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Example 18
Solubility of 2,2'-Dithio-Bis-Ethane Sulfonate In Sterile Water

In this example, 10 grams of the disodium salt of 2,2'-dithio-bis-ethane sulfonate was dissolved in 50 ml of sterile HPLC grade water and the pH of the solution was readjusted to a pH of 7.0 using 1N hydrochloric acid. The resulting solution was then passed through a 0.2 micron syringe filter into an autoclaved round bottom flask (250 ml). This sterile solution was then freeze dried (lyophilized) to a white crystalline powder. The lyophilized powder was then used for the following solubility studies.

1 ml of sterile HPLC grade water was distributed in each of ten sterilized 10 ml vials. As described in FIG. 6 below, varying amounts of the lyophilized disodium salt of 2,2'-dithio-bis-ethane sulfonate were then added to each vial. Each vial was first observed at room temperature for a period of approximately 15 minutes, and then heated to a temperature of 37° C. for a period of at least 15 minutes. The Table below demonstrates that, based on the tyndall effect observed in each vial, 2,2'-dithio-bis-ethane sulfonate is soluble in concentrations ranging from about 10.5 mg per ml to about 102 mg per ml.

Solubility of 2,2'-dithio-bis-ethane sulfonate (BNPI 7787) in sterile water at 37° C.

| Entry No. | Qty. of BNPI 7787 (mg) | Vol. of Sterile water (ml) | Incubation time (min.) | Observation at 25° C. | Observation at 37° C. |
|---|---|---|---|---|---|
| 1 | 10.50 | 1 | 15 | Clear | Clear |
| 2 | 20.50 | 1 | 15 | Clear | Clear |
| 3 | 45.50 | 1 | 15 | Clear | Clear |
| 4 | 51.65 | 1 | 15 | Clear | Clear |
| 5 | 69.13 | 1 | 15 | Slight yndall | Clear |
| 6 | 94.33 | 1 | 15 | Tyndall | Clear |
| 7 | 98.63 | 1 | 15 | Tyndall | Clear after 30 min. |
| 8 | 102.83 | 1 | 15 | Tyndall | Clear after 360 min. |

Example 19

Solubility of 2,2'-Dithio-Bis-Ethane Sulfonate in Sterile Water and 0.9% Sodium Chloride Solution For this example, 10 grams of the disodium salt of 2,2'-dithio-bis-ethaiie sultonate BNPI7787) was dissolved in 50 ml of sterile HPLC grade water and the pH of the solution was readjusted to a pH of 7.15 using 1N hydrochloric acid. The resulting solution was then passed through a 0.2 micron syringe filter into an autoclaved round bottom flask (250 ml). This sterile solution was then freeze dried (lyophilized) to a white crystalline powder. The lyophilized powder was then used for the following solubility studies.

1 ml of sterile HPLC grade water was distributed in each of one set of six sterilized 10 ml vials. 1 ml of 0.9% sodium chloride solution was then distributed in each of a second set of six sterilized 10 ml vials. The 0.9% sodium chloride solution was obtained by dissolving 9 mg of USP grade sodium chloride in sterile HPLC grade water using an agitator. As described in the table below, varying amounts of the lyophilized disodium salt of 2,2'-dithio-bis-ethane sulfonate were then added to each of the 12 vials. Each vial was first observed at room temperature for a period of approximately 15 minutes and then heated to a temperature of 37° C. for a period of at least 15 minutes. The table below demonstrates that, based on the tyndall effect observed in each vial, 2,2'-dithio-bis-ethane sulfonate is soluble in sterile water and in sodium chloride solution in concentrations of 2,2'-dithio-bis-ethane sulfonate ranging from about 100 mg per ml to about 320 mg per ml.

Solubility of 2,2'-dithio-bis-ethane sulfonate in sterile water and NaCl solution at 37° C. & pH 7.15

| Entry No. | Qty. of BNPI 7787 (mg) | Sterile water (ml) | 0.9% NaCl soln. (ml) | Observation at 25° C. | Observation at 37° C. |
|---|---|---|---|---|---|
| 1 | 100 | 1 | 0 | Clear | Clear |
| 2 | 100 | 0 | 1 | Clear | Clear |
| 3 | 200 | 1 | 0 | Clear | Clear |
| 4 | 200 | 0 | 1 | Clear | Clear |
| 5 | 300 | 1 | 0 | Clear | Clear |
| 6 | 300 | 0 | 1 | Clear | Clear |
| 7 | 320 | 1 | 0 | Clear | Clear |
| 8 | 320 | 0 | 1 | Slight tydall | Clear |
| 9 | 350 | 1 | 0 | Not clear | Clear |
| 10 | 350 | 0 | 1 | Not Clear | Not clear |
| 11 | 400 | 1 | 0 | Not Clear | Not clear |
| 12 | 400 | 0 | 1 | Not Clear | Not clear |

REFERENCES

Brock, N., et al., Studies on the Urotoxicity of Oxazaphosphorine Cytostatics and its Prevention, Eur. J. Cancer Clin. Oncol., 17:1155–1163, 1981.

Brock, N., et al., Studies on the Urotoxicity of Oxazaphosphorine Cytostatics and its Prevention -III. Profile of Action of Sodium 2-mercaptoethane Sulfonate (Mesna). Eur J. Cancer Clin. Oncol. 18(12): 1377–1387, 1982.

Brock, N., et al. Arzneim Forsch 32:486–487 (1982).

Brock, N., et al., Pharmacokinetics and Mechanism of Action of Detoxifying Low-Molecular-Weight Thiols. J Cancer Res. Clin. Oncol. 108:87–97, 1984.

Burkert, H., et al., Bioavailability of Orally Administered Mesna. Arzneim.-Forsch./Drug Res. 34:(11), 1597, 1984.

Campbell, A. B., et al., Plasma platinum levels: Relationship to cisplatin dose and nephrotoxicity. Cancer Treat. Rep., 67, 169, 1983.

Choie, D. D., et al., Acute and chronic cisplatin nephropathy in rats. Lab. Invest., 44, 397, 1981.

Eastman, A., Reevaluation of interaction of cis-dichloro (ethylenediamine) platinum (II) with DNA. Biochemistry, 25:3912, 1986.

Gonzalez-Vitale, J. C., et al., The renal pathology in clinical trials of cisplatin (II) diamminedichloride. Cancer, 39, 1362, 1977.

Hanigan, M. H. et al., Inhibition of gamma-Glutamyl Transpeptidase Activity by Acivicin In Vivo Protects the Kidney from Cisplatin-Induced Toxicity. Cancer Research 54, 5925, 1995.

Hayes, D. M., et al., High dose cisplatin diammine dichloride, amelioration of renal toxicity by mannitol diuresis. Cancer, 39, 1372, 1977.

Howell, S. B., Intraperitoneal cisplatin with systemic thiosulfate protection, Ann. Int. Med., 97, 845–851, 1982.

Kelley, S. L., et al., Overexpression of metallothionein confers resistance to anticancer drugs. Science, 241:1813, 1988.

Kempf, S. R., et al., Effective prevention of the nephrotoxicity of cisplatin (CDDP) by administration of sodium 2-mercaptoethane-sulfonate (mesna) in rats. Br. J. Cancer, 52:937–939, 1985.

Kociba, R. J., et al., Acute toxicologic and pathologic effects of cis-diammine-dichloro-platinum in the male rat. Cancer Chemother. Rep., 55, 1, 1971.

Lemaire, L. and Reiger, M., Synthesis of 2-mercaptoethane sulfonamide, J. Org. Chem. 26, 1330–1, 1961.

Offerman, J. J. G., et al., Acute effects of cis-diamminedichloroplatinwn (CDDP) on renalfunction. Cancer Chemother. Pharmacol., 12, 36, 1984.

Ormstad et al., Cancer Research, 43:333, 1983.

Ostrow, S., et al., High-dose cisplatin therapy using mannitol versus furosemide diuresis: comparative pharmacokinetics and toxicity. Cancer Treat. Rep., 65, 73, 1981.

Ozols, R. F., et al., High-dose cisplatin in hypertonic saline. Ann. Intern. Med., 100, 19, 1984.

Perry, M. C., The Chemotherapy Source Book, Williams and Wilkins, 1172 pp., 1992.

Physician's Desk Reference, 661, 1994 Edition, Medical Economics Data Production Company.

Pinto, A. L., et al., Binding of the antitumour drug cis-diamminedichloroplatinum(II) (cisplatin) to DNA. Biochem. Biophys. Acta. 780:167, 1985.

Pohl, et al. Meth. Find. Clin. Pharmacol. 3(Suppl 1):95–101, 1981.

Rozenzweig, M., et al., cis-diamminedichloroplatinwn (II). Ann. Intern. Med., 86, 803, 1977.

Sidau. B. and Shaw, I. C., Determination of sodium 2-mercaptoethane sulfonate by high performance liquid chromatography using post-column reaction calorimetry or electrochemical detection, *Journal of Chromatography*, 311, 234–238, 1984.

Shaw, I. C. and Weeks, M. S., *Eur J Cancer Clin Oncology* 23:933–935; 1987.

U.S. Pat. No. 4,310,515, entitled "Pharmaceutical Compositions of Cisplatin," Issued Jan. 12, 1982.

The foregoing description has been directed to particular embodiments of the invention in accordance with the requirements of the Patent Statues for the purposes of illustration and explanation. It will be apparent, however, to those skilled in this art, that many modifications, changes, and variations in the claimed solutions and methods set forth will be possible without departing from the scope and spirit of the claimed invention. It is intended that the following claims be interpreted to embrace all such modifications, changes, and variations.

What is claimed is:

1. A pharmaceutical formulation comprising 2,2'-dithio-bis-ethane sulfonate, or a pharmaceutically acceptable salt thereof, and cis-diammine dichloro platinum, wherein said pharmaceutical formulation is in lyophilized form and is dissolved prior to administration to a human patient with cancer.

2. A pharmaceutical formulation comprising cis-diammine dichloro platinum, lyophilized 2,2'-dithio-bis-ethane sulfonate, or a pharmaceutically acceptable salt thereof, and sodium chloride, wherein said cis-diammine dichloro platinum and lyophilized 2,2'-dithio-bis-ethane sulfonate or a pharmaceutically acceptable salt thereof are dissolved prior to intravenous administration with a pharmaceutically acceptable aqueous diluent at a pH range of 2.0 to 6.0.

3. The lyophilized composition of claim 2 further containing a buffer selected from the group consisting of sodium acetate and phosphate.

* * * * *